United States Patent [19]

Majarian et al.

[11] Patent Number: 6,130,082
[45] Date of Patent: Oct. 10, 2000

[54] RECOMBINANT FLAGELLIN VACCINES

[75] Inventors: William R. Majarian, Mt. Royal, N.J.; Bruce A. D. Stocker, Palo Alto; Salete M. C. Newton, Mountain View, both of Calif.

[73] Assignees: American Cyanamid Company, Madison, N.J.; The Board of Trustees of the Leland Stanford Junior University, Stanford, Calif.

[21] Appl. No.: 07/837,668

[22] Filed: Feb. 14, 1992

Related U.S. Application Data

[63] Continuation of application No. 07/348,430, May 5, 1989, abandoned, which is a continuation-in-part of application No. 07/190,570, May 5, 1988, abandoned.

[51] Int. Cl.[7] .............. C12N 1/21; C12N 15/62; C12N 15/00; A61K 39/116
[52] U.S. Cl. ............ 435/252.3; 536/23.4; 536/23.7; 435/320.1; 435/252.33; 424/192.1; 424/200.1; 424/258.1; 424/93.2
[58] Field of Search ............... 435/172.3, 320.1, 435/252.3, 69.1, 69.3, 69.7, 252.33, 254.11, 257.2; 424/88, 92, 93 A, 192.1, 200.1, 201.1, 93.2, 258.1; 935/47, 48, 65, 72; 536/23.4, 23.7

[56] References Cited

U.S. PATENT DOCUMENTS

| | | | |
|---|---|---|---|
| 4,691,006 | 9/1987 | Stevens | 530/324 |
| 4,702,911 | 10/1987 | McMichael | 424/242.1 |
| 4,801,536 | 1/1989 | Stahl et al. | 435/69.1 |
| 4,857,637 | 8/1989 | Hammonds et al. | 424/185.1 |
| 4,882,145 | 11/1989 | Thornton et al. | 424/189.1 |
| 4,886,748 | 12/1989 | Asaka et al. | 435/69.7 |
| 4,888,170 | 12/1989 | Curtiss | 424/200.1 |
| 4,963,354 | 10/1990 | Shepard et al. | 424/85.1 |

FOREIGN PATENT DOCUMENTS

| | | |
|---|---|---|
| 184086 | 6/1986 | European Pat. Off. . |
| 237045 | 9/1987 | European Pat. Off. . |
| 8600911 | 2/1986 | WIPO ........................... 514/12 |
| WO87/02385 | 4/1987 | WIPO . |
| WO87/06590 | 11/1987 | WIPO . |

OTHER PUBLICATIONS

Jolivet, M.E. et al., *Infection and Immunity* 55:1498–1502 (1987).

Kennedy, R.C. et al., *Science* 231:1556–1559 (1986).

Jacob, C.O. et al., *Proc. Natl. Acad. Sci. USA* 80 7611–7615 (1983).

Newton, S.M.C. et al., *Science* 244:70–72 (Apr. 1989).

(List continued on next page.)

*Primary Examiner*—Mary E. Mosher
*Attorney, Agent, or Firm*—Hamilton, Brook, Smith & Reynolds, P.C.

[57] ABSTRACT

The present invention is directed to recombinant genes and their encoded proteins which are recombinant flagellin fusion proteins. Such fusion proteins comprise amino acid sequences specifying an epitope encoded by a flagellin structural gene and an epitope of a heterologous organism which is immunogenic upon introduction of the fusion protein into a vertebrate host. The recombinant genes and proteins of the present invention can be used in vaccine formulations, to provide protection against infection by the heterologous organism, or to provide protection against conditions or disorders caused by an antigen of the organism. In a specific embodiment, attenuated invasive bacteria expressing the recombinant flagellin genes of the invention can be used in live vaccine formulations. The invention is illustrated by way of examples in which epitopes of malaria circumsporozoite antigens, the B subunit of Cholera toxin, surface and presurface antigens of Hepatitis B. VP7 polypeptide of rotavirus, envelope glycoprotein of HIV, and M protein of Streptococcus, are expressed in recombinant flagellin fusion proteins which assemble into functional flagella, and which provoke an immune response directed against the heterologous epitope, in a vertebrate host.

3 Claims, 17 Drawing Sheets

OTHER PUBLICATIONS

Clements, J.D., et al., "Oral Immunization of Mice with Attenuated *Salmonella enteritidis* Containing a Recombinant Plasmid Which Codes for Production of the B Subunit of Heat–Labile *Escherichia coli* Enterotoxin", *Infection and Immunity*, 53(6): 685–692 (1986).

Tizard, I.R. 1984, Immunology: An Introduction Saunders College Publishing, Philadelphia PA, pp. 14–18 and 22–24.

Mandelstar, J. et al. 1982, Biochemistry of Bacterial Growth, third edition. John Wiley & Sons, NY, p. 365.

Kuwajima, G. 1988, *J. Bacteriol.* vol 179 pp. 485–488.

Kuwajima, G. et al. 1988. *Bio/Technology* vol 6 pp. 1080–1089.

Charbit, A. et al. 1987. *J. Immunol.* vol 139 pp. 1658–1664.

Charbit, A. et al. 1988. *Ann. Inst. Pasteur/Microbiol.* vol. 139 pp. 45–58.

Dougan, G. et al. 1987, *Parasite Immunol.* vol 9 pp. 151–160.

Anderson, P. 1983 *Infection and Immunity,* vol 39 pp. 233–238.

Hilleman, M. R. 1988. *Human Retroviruses, Cancer, and AIDS: approaches to prevention and therapy.* Alan R. Liss, pp. 291–311.

Matthews, T.J. et al. 1988. *Human Retroviruses, Cancer, and AIDS: approaches to prevention and therapy.* Alan R. Liss pp. 313–325.

Macnab, R.M., 1987. "Flagella", In: *Escherichia coli* and *Salmonella Typhimurium,* Ed. Neidhardt, F.C. et al, American Society for Microbiology, pp. 70–83.

Wei, L.N. et al. 1985, Journal of Molecular Biology, vol. 186, pp. 791–803.

Eichinger, D.J. et al. 1986. Molecular and Cellular Biology, vol. 6 pp. 3965–3972.

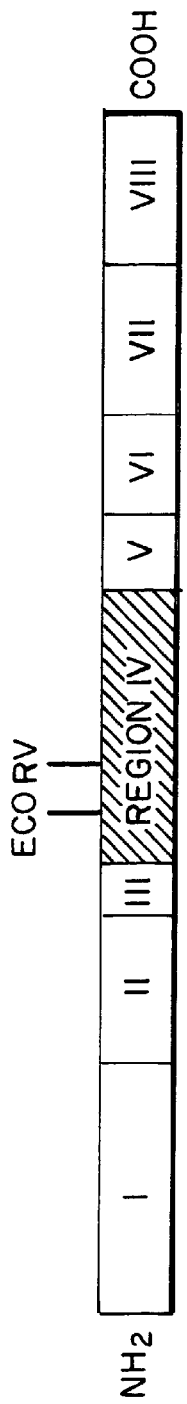
```
       V    E    V    P    Q    S    G    H    I    D    S    Q    K    K    A
5' - GTT GAA GTT CCG GGT AGC CAG CAC ATC GAT AGC CAG AAG AAG GCT - 3'
3' - CAA CTT CAA GGC CCA TCG GTC GTG TAG CTA TCG GTC TTC TTC CGA - 5'
```
FIG. 4B

FIGURE 2B

|     |     |     |     |     |     |     |     |     |     |     |     |     |     |
|-----|-----|-----|-----|-----|-----|-----|-----|-----|-----|-----|-----|-----|-----|
|     | M   | A   | Q   | V   | I   | N   | T   | N   | S   | L   | S   | L   | L   |
| 1   | ATG | GCA | CAA | GTC | ATT | AAT | ACA | AAC | AGC | CTG | TCG | CTG | TTG | 39 |

|     | T   | Q   | N   | N   | L   | N   | K   | S   | Q   | S   | A   | L   | G   |     |
|-----|-----|-----|-----|-----|-----|-----|-----|-----|-----|-----|-----|-----|-----|-----|
| 40  | ACC | CAG | AAT | AAC | CTG | AAC | AAA | TCC | CAG | TCC | GCT | CTG | GGC | 78 |

|     | T   | A   | I   | E   | R   | L   | S   | S   | G   | L   | R   | I   | N   |     |
|-----|-----|-----|-----|-----|-----|-----|-----|-----|-----|-----|-----|-----|-----|-----|
| 79  | ACC | GCT | ATC | GAG | CGT | CTG | TCT | TCC | GGT | CTG | CGT | ATC | AAC | 117 |

|     | S   | A   | K   | D   | D   | A   | A   | G   | Q   | A   | I   | A   | N   |     |
|-----|-----|-----|-----|-----|-----|-----|-----|-----|-----|-----|-----|-----|-----|-----|
| 118 | AGC | GCG | AAA | GAC | GAT | GCG | GCA | GGT | CAG | GCG | ATT | GCT | AAC | 156 |

|     | R   | F   | T   | A   | N   | I   | K   | G   | L   | T   | Q   | A   | S   |     |
|-----|-----|-----|-----|-----|-----|-----|-----|-----|-----|-----|-----|-----|-----|-----|
| 157 | CGT | TTC | ACC | GCG | AAC | ATC | AAA | GGT | CTG | ACT | CAG | GCT | TCC | 195 |

|     | R   | N   | A   | N   | D   | G   | I   | S   | I   | A   | Q   | T   | T   |     |
|-----|-----|-----|-----|-----|-----|-----|-----|-----|-----|-----|-----|-----|-----|-----|
| 196 | CGT | AAC | GCT | AAC | GAC | GGT | ATC | TCC | ATT | GCG | CAG | ACC | ACT | 234 |

|     | E   | G   | A   | L   | N   | E   | I   | N   | N   | N   | L   | Q   | R   |     |
|-----|-----|-----|-----|-----|-----|-----|-----|-----|-----|-----|-----|-----|-----|-----|
| 235 | GAA | GGC | GCG | CTG | AAC | GAA | ATC | AAC | AAC | AAC | CTG | CAG | CGT | 273 |

|     | V   | R   | E   | L   | A   | V   | Q   | S   | A   | N   | G   | T   | N   |     |
|-----|-----|-----|-----|-----|-----|-----|-----|-----|-----|-----|-----|-----|-----|-----|
| 274 | GTG | CGT | GAA | CTG | GCG | GTT | CAG | TCT | GCT | AAC | GGT | ACT | AAC | 312 |

|     | S   | Q   | S   | D   | L   | D   | S   | I   | Q   | A   | E   | I   | T   |     |
|-----|-----|-----|-----|-----|-----|-----|-----|-----|-----|-----|-----|-----|-----|-----|
| 313 | TCC | CAG | TCT | GAC | CTT | GAC | TCT | ATC | CAG | GCT | GAA | ATC | ACC | 351 |

|     | Q   | R   | L   | N   | E   | I   | D   | R   | V   | S   | G   | Q   | T   |     |
|-----|-----|-----|-----|-----|-----|-----|-----|-----|-----|-----|-----|-----|-----|-----|
| 352 | CAG | CGT | CTG | AAC | GAA | ATC | GAC | CGT | GTA | TCC | GGT | CAG | ACT | 390 |

|     | Q   | F   | N   | G   | V   | K   | V   | L   | A   | Q   | D   | N   | T   |     |
|-----|-----|-----|-----|-----|-----|-----|-----|-----|-----|-----|-----|-----|-----|-----|
| 391 | CAG | TTC | AAC | GGC | GTG | AAA | GTC | CTG | GCG | CAG | GAC | AAC | ACC | 429 |

|     | L   | T   | I   | Q   | V   | G   | A   | N   | D   | G   | E   | T   | I   |     |
|-----|-----|-----|-----|-----|-----|-----|-----|-----|-----|-----|-----|-----|-----|-----|
| 430 | CTG | ACC | ATC | CAG | GTT | GGT | GCC | AAC | GAC | GGT | GAA | ACT | ATT | 468 |

|     | D   | I   | D   | L   | K   | E   | I   | S   | S   | K   | T   | L   | G   |     |
|-----|-----|-----|-----|-----|-----|-----|-----|-----|-----|-----|-----|-----|-----|-----|
| 469 | GAT | ATT | GAT | TTA | AAA | GAA | ATT | AGC | TCT | AAA | ACA | CTG | GGA | 507 |

FIGURE 2C

```
         L   D   K   L   N   V   Q   D   A   Y   T   P   K
508      CTT GAT AAG CTT AAT GTC CAG GAT GCC TAC ACC CCG AAA      546

E   T   A   V   T   V   D   K   T   T   Y   K   N
547      GAA ACT GCT GTA ACC GTT GAT AAA ACT ACC TAT AAA AAT      585

G   T   D   T   I   T   A   Q   S   N   T   D   I
586      GGT ACA GAT ACT ATT ACA GCC CAG AGC AAT ACT GAT ATC      624

Q   T   A   I   G   G   G   A   T   G   V   T   G
625      CAA ACT GCA ATT GGC GGT GGT GCA ACG GGG GTT ACT GGG      663

A   D   I   K   F   K   D   G   Q   Y   Y   L   D
664      GCT GAT ATC AAA TTT AAA GAT GGT CAA TAC TAT TTA GAT      702

V   K   G   G   A   S   A   G   V   Y   K   A   T
703      GTT AAA GGC GGT GCT TCT GCT GGT GTT TAT AAA GCC ACT      741

Y   D   E   T   T   K   K   V   N   I   D   T   T
742      TAT GAT GAA ACT ACA AAG AAA GTT AAT ATT GAT ACG ACT      780

D   K   T   P   L   A   T   A   E   A   T   A   I
781      GAT AAA ACT CCG TTA GCA ACT GCG GAA GCT ACA GCT ATT      819

R   G   T   A   T   I   T   H   N   Q   I   A   E
820      CGG GGA ACG GCC ACT ATA ACC CAC AAC CAA ATT GCT GAA      858

V   T   K   E   G   V   D   T   T   T   V   A   A
859      GTA ACA AAA GAG GGT GTT GAT ACG ACC ACA GTT GCG GCT      897

Q   L   A   A   A   G   V   T   G   A   D   K   D
898      CAA CTT GCT GCT GCA GGG GTT ACT GGT GCC GAT AAG GAC      936

N   T   S   L   V   K   L   S   F   E   D   K   N
937      AAT ACT AGC CTT GTA AAA CTA TCG TTT GAG GAT AAA AAC      975

G   K   V   I   D   G   G   Y   A   V   K   M   G
976      GGT AAG GTT ATT GAT GGT GGC TAT GCA GTG AAA ATG GGC      1014
```

FIGURE 2D

```
          D   D   F   Y   A   A   T   Y   D   E   K   Q   V
1015     GAC GAT TTC TAT GCC GCT ACA TAT GAT GAG AAA CAG GTA    1053

Q   L   L   L   N   N   H   Y   T   D   G   A   G
1054     CAA TTA CTG CTA AAC AAC CAC TAT ACA GAT GGT GCT GGC    1092

V   L   Q   T   G   A   V   K   F   G   G   A   N
1093     GTG CTC CAA ACT GGA GCT GTG AAA TTT GGT GGC GCA AAT    1131

G   K   S   E   V   V   T   A   T   V   G   K   T
1132     GGT AAA TCT GAA GTT GTT ACT GCT ACC GTA GGT AAA ACT    1170

Y   L   A   S   D   L   D   K   H   N   F   R   T
1171     TAC TTA GCA AGC GAC CTT GAC AAA CAT AAC TTC AGA ACA    1209

G   G   E   L   K   E   V   N   T   D   K   T   E
1210     GGC GGT GAG CTT AAA GAG GTT AAT ACA GAT AAG ACT GAA    1248

N   P   L   Q   K   I   D   A   A   L   A   Q   V
1249     AAC CCA CTG CAG AAA ATT GAT GCT GCC TTG GCA CAG GTT    1287

D   T   L   R   S   D   L   G   A   V   Q   N   R
1288     GAT ACA CTT CGT TCT GAC CTG GGT GCG GTA CAG AAC CGT    1326

F   N   S   A   I   T   N   L   G   N   T   V   A
1327     TTC AAC TCC GCT ATC ACC AAC CTG GGC AAT ACC GTA AAT    1365

N   L   S   S   A   R   S   R   I   E   D   S   D
1366     AAC CTG TCT TCT GCC CGT AGC CGT ATC GAA GAT TCC GAC    1404

Y   A   T   E   V   S   N   M   S   R   A   Q   I
1405     TAC GCG ACC GAA GTC TCC AAC ATG TCT CGC GCG CAG ATT    1443

L   Q   Q   A   G   T   S   V   L   A   Q   A   N
1444     CTG CAG CAG GCC GGT ACC TCC GTT CTG GCG CAG GCT AAC    1482

Q   V   P   Q   N   V   L   S   L   L   R   *
1483     CAG GTT CCG CAA AAC GTC CTC TCT TTA CTG CGT TAA        1518
```

FIGURE 3A

```
       N    P    A    N    P    N    A    N    P    N    A
5'-AAT CCG  AAC  GCT  AAC  CCG  AAC  GCT  AAC  CCG  AAC  GCG -3'
3'-    GGC  TTG  CGA  TTG  GGC  TTG  CGA  TTG  GGC  TTG  CGC  TTA-5'
       N    P    N    A    N    P    N    A    N    P    N    A
```

FIGURE 3B

```
       D    P    A    P    P    N    A    N    D    P    A    P    P    N    A    N
5'-GAC CCA  GCA  CCA  CCA  AAC  GCA  AAT  GAC  CCA  GCA  CCA  CCA  AAC  GCA  AAT -3'
3'-    GGT  CGT  GGT  GGT  TTG  CGT  TTA  CTG  GGT  CGT  GGT  GGT  TTG  CGT  TTA  CTG-5'
```

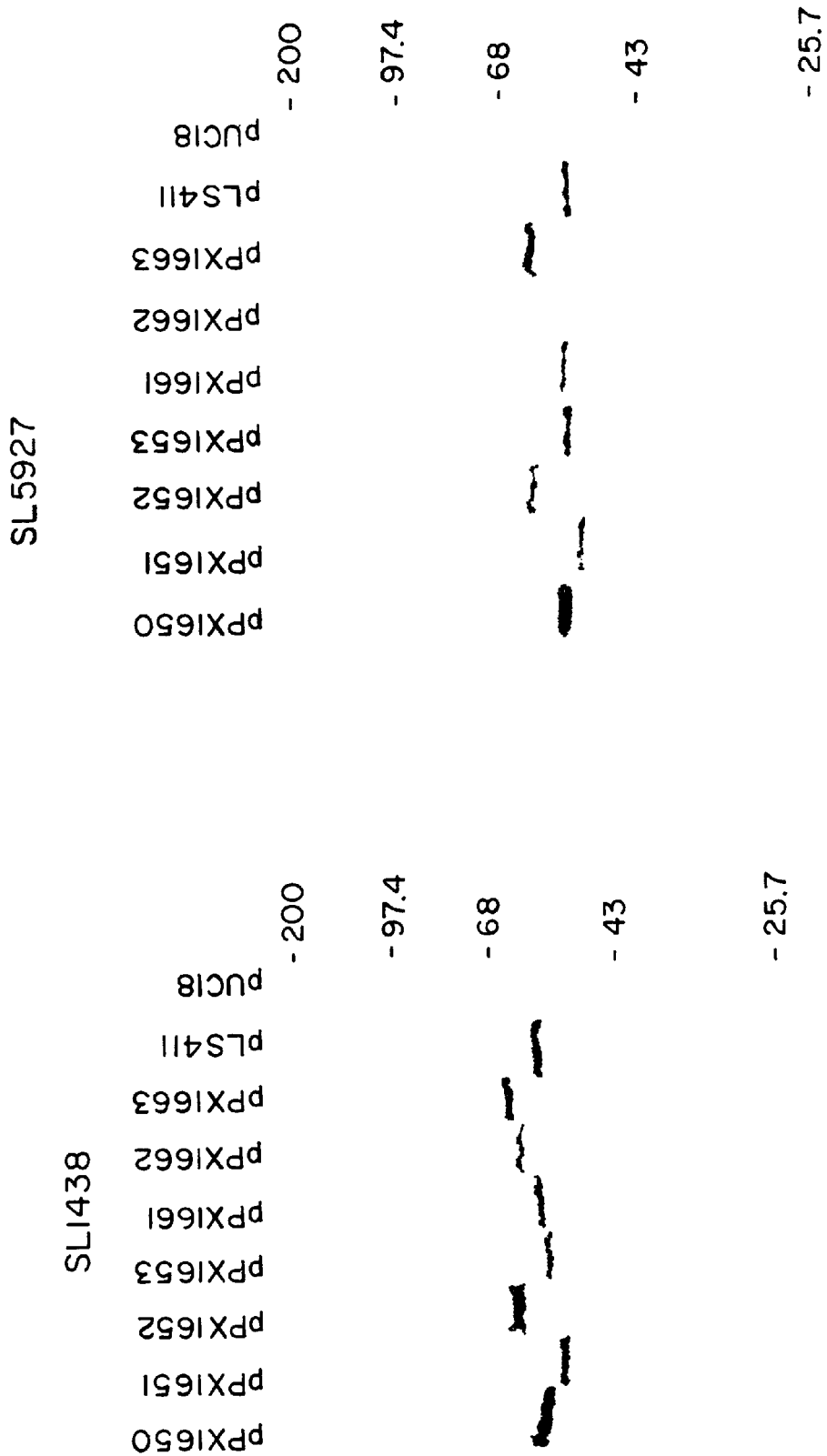

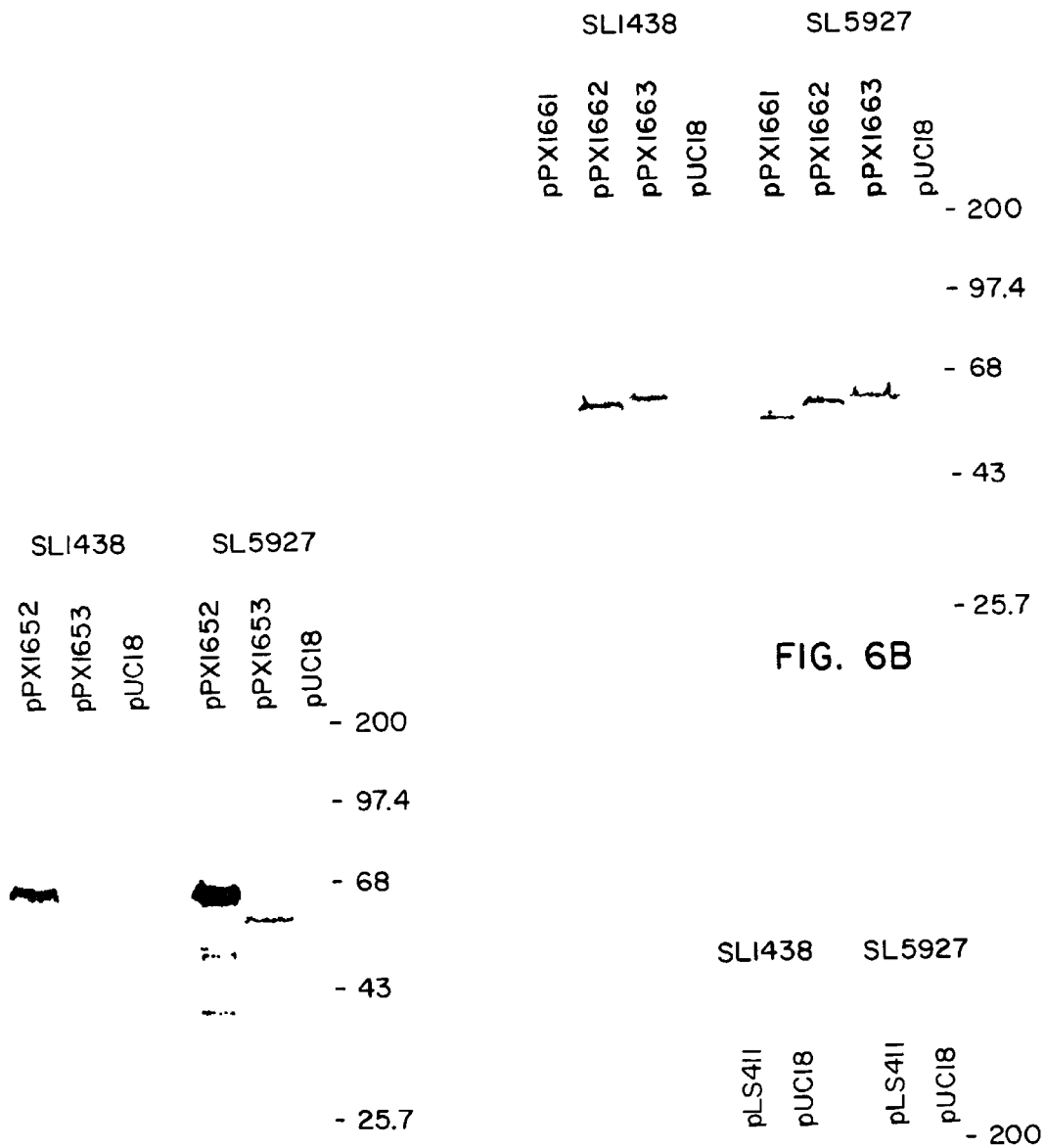
FIG. 6B
FIG. 6C
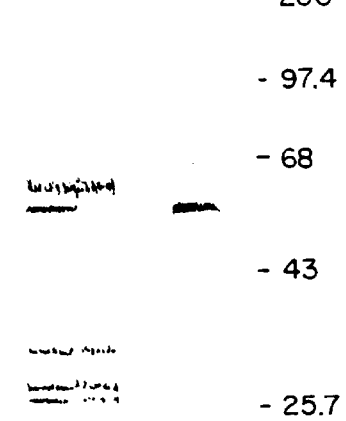
FIG. 6D

S 122-137 (ayw)

```
                                    KpnI
5'CGT ACC TGT ATG ACC ACC GCT CAG GGT ACC TCT ATG TAC
      TAC TGG TGG CGA GTC CCA TGG AGA TAC ATG GGC AGG ACA
 ARG THR CYS MET THR THR ALA GLN GLY THR SER MET TYR PRO SER CYS
```

PreS2 120-145(ayw)

```
                                                    BamHI
5'ATG CAG TGG AAC AGC ACC ACC TTC CAC CAG ACC CTA CAG GAT CCG CGT
   TAC GTC ACC TTG TCG TGG TGG AAG GTG GTC TGG GAT GTC CTA GGC GCA
 MET GLN TRP ASN SER THR THR PHE HIS GLN THR LEU GLN ASP PRO ARG
                                    EcoRV
 GTT CGT GGT CTA TAT TTC CCG GCT GGT GGT    3'
 CAA GCA CCA GAT ATA AAG GGC CGA CCA CCA CTA
 VAL ARG GLY LEU TYR PHE PRO ALA GLY GLY ASP
```

Map of flagellin gene (HI-d)

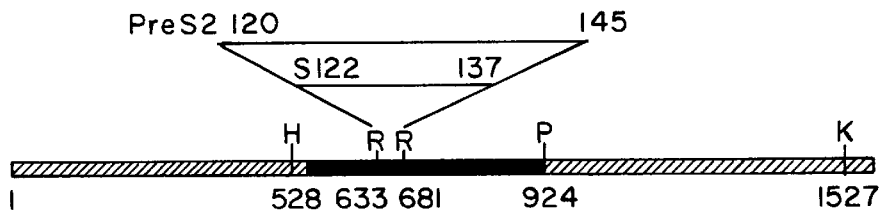

FIG. 10

RECOMBINANT FLAGELLIN VACCINES

RELATED APPLICATIONS

This is a continuation of application Serial No. 07/348,430 filed on May 5, 1989, now abandoned, which is a Continuation-in-Part of 07/190,570 filed May 5, 1988, now abandoned.

BACKGROUND OF THE INVENTION

Recombinant DNA Technology and Gene Expression

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. Several general methods have been developed which enable construction of recombinant DNA molecules.

Regardless of the method used for construction, the recombinant DNA molecule must be compatible with the host cell, i.e., capable of autonomous replication in the host cell or stably integrated into one or more of the host cell's chromosomes or plasmids. The recombinant DNA molecule should preferably also have a marker function which allows the selection of the desired recombinant DNA molecule(s). In addition, if all of the proper replication, transcription, and translation signals are correctly arranged on the recombinant vector, the foreign gene will be properly expressed in, e.g., the transformed bacterial cells, in the case of bacterial expression plasmids, or in permissive cell lines or hosts infected with a recombinant virus or carrying a recombinant plasmid having the appropriate origin of replication.

Different genetic signals and processing events control levels of gene expression such as DNA transcription and messenger RNA (mRNA) translation. Transcription of DNA is dependent upon the presence of a promoter, which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and furthermore, procaryotic promoters are not recognized and do not function in eucaryotic cells.

Similarly, translation of mRNA in procaryotes depends upon the presence of the proper procaryotic signals, which differ from those of eucaryotes. Efficient translation of mRNA in procaryotes requires a ribosome binding site called the Shine-Dalgarno (S/D) sequence (Shine, J. and Dalgarno, L., 1975, *Nature* 254:34–38) on the mRNA. This sequence is a short nucleotide sequence of mRNA that is located before the start codon, usually AUG, which encodes the amino-terminal (formyl-) methionine of the protein. The S/D sequences are complementary to the 3' end of the 16S rRNA (ribosomal RNA), and probably promote binding of mRNA to ribosomes by duplexing with the rRNA to allow correct positioning of the ribosome (Shine, J. and Dalgarno, L., 1975, *Nature* 254:34–38).

Successful expression of a cloned gene requires sufficient transcription of DNA, translation of the mRNA, and in some instances, post-translational modification of the protein. Expression vectors have been used to express genes under the control of an active promoter in a suitable host, and to increase protein production.

Vaccines

The development of vaccines for the prevention of viral, bacterial, fungal or parasitic diseases is the focus of much research effort.

Traditional ways of preparing vaccines include the use of inactivated or attenuated pathogens. A suitable inactivation of the pathogenic microorganism renders it harmless as a biological agent but does not destroy its immunogenicity. Injection of these "killed" particles into a host will then elicit an immune response capable of preventing a future infection with a live microorganism. However, a major concern in the use of killed vaccines (using inactivated pathogen) is failure to inactivate all the microorganism particles. Even when this is accomplished, since killed pathogens do not multiply in their host, or for other unknown reasons, the immunity achieved is often incomplete, short lived and requires multiple immunizations. Finally, the inactivation process may alter the microorganism's antigens, rendering them less effective as immunogens.

Attenuation refers to the production of strains of pathogenic microorganisms which have essentially lost their disease-producing ability. One way to accomplish this is to subject the microorganism to unusual growth conditions and/or frequent passage in cell culture. Mutants are then selected which have lost virulence but yet are capable of eliciting an immune response. Attenuated pathogens often make good immunogens as they actually replicate in the host cell and elicit long lasting immunity. However, several problems are encountered with the use of live vaccines, the most worrisome being insufficient attenuation and the risk of reversion to virulence.

An alternative to the above methods is the use of subunit vaccines. This involves immunization only with those components which contain the relevant immunological material.

Vaccines are often formulated and inoculated with various adjuvants. The adjuvants aid in attaining a more durable and higher level of immunity using smaller amounts of antigen or fewer doses than if the immunogen were administered alone. The mechanism of adjuvant action is complex and not completely understood. However, it may involve the stimulation of cytokine production, phagocytosis and other activities of the reticuloendothelial system as well as a delayed release and degradation of the antigen. Examples of adjuvants include Freund's adjuvant (complete or incomplete), Adjuvant 65 (containing peanut oil, mannide monooleate and aluminum monostearate), the pluronic polyol L-121, Avridine, and mineral gels such as aluminum hydroxide, aluminum phosphate, etc. Freund's adjuvant is no longer used in vaccine formulations for humans because it contains nonmetabolizable mineral oil and is a potential carcinogen.

Live, attenuated Salmonella have been demonstrated to be capable of stimulating a protective immune response against challenge with the homologous, virulent strain (Germanier, R. and Furer, E., 1975, *J. Infect Dis.* 181:533; Germanier, R., 1984, in *Bacterial Vaccines*, Academic Press, N.Y., pp. 137–165; Levine, M. M., et al., 1983, *Microbiol. Rev.* 47:510; Wahdan, M. H., et al., 1982, *J. Infect. Dis.* 145:292; Hoiseth, S. K. and Stocker, B. A. D., 1981, *Nature* 291:238; Stocker, B. A. D., et al. 1982, *Dev. Biol. Std.* 53:47; Lindberg, A. A. and Robertsson, J. A., 1983, *Infect. Immun.* 41:751; Robertsson, J. A., et al., 1983, *Infect. Immun.* 41:742; Smith, B. P., et al., 1984, *Am. J. Vet. Res.* 45:2231; Smith, B. P., et al., 1984, *Am. J. Vet. Res.* 45:59; Moser, I., et al., 1980, *Med. Microbiol. Imm.* 168:119). In addition, several investigators have utilized attenuated Salmonella harboring plasmids encoding foreign antigens to deliver these foreign antigens to the immune system (Formal, S. B., et al., 1981, *Infect. Immun.* 34:746; U.S. Pat. No. 4,632,830 by Formal et al.; Clements, J. D., et al., 1986, *Infect. Immun.* 53:685; Maskell, D. J., et al., 1987, *Microb. Path.* 2:211; Brown, A., et al., 1987, *J. Infect. Dis.* 155:86; Dougan, G., et al., 1987, *Parasite Immun.* 9:151).

The repeating immunodominant epitope associated with the circumsporozoite protein of Plasmodium species is considered the target for protective humoral (and possible cell-mediated) responses against malaria sporozoites (Miller, L. H., et al., 1986, *Science* 234:1349); monoclonal antibodies have been described which recognize these molecules and are able to passively protect naive recipient animals. Two vaccines based on these repeating epitopes have been tested in humans, and have been shown to induce a protective immune response in some individuals (Ballou, W. R., et al., 1987, *Lancet* i:1277; Herrington, D., et al., 1987, *Nature* 328:257).

Cholera toxin is the prototype of a family of bacterial enterotoxins which mediate diarrheal disease and are related in structure, function and immunogenicity. Other members of this family include the heat-labile toxin of *E. coli* isolated from humans (Yamamoto, T. and Yokota, T., 1983, *J. Bacteriology* 155:728) and from pigs (Leong, J., et al., 1985, *Infect. Immun.* 48:73), and toxins from *Salmonella typhimurium* (Finkelstein, R. A., et al., 1983, *FEMS Microbiology Letters* 17:239) and from *Campylobacter jejuni* (Walker, R. I., et al., 1986, *Microbiology Rev.* 50:81). Common to all of these toxins is an A subunit which mediates ADP-ribosyltransferase activity, resulting in the activation of adenylate cyclase, ultimately leading to death of the target cell. In addition, all of these toxins contain an immunologically dominant B subunit which mediates binding of the holotoxin to the target cell. The B subunit by itself is non-toxic, and immunization with this molecule induces the formation of toxin-neutralizing antibodies.

Vaccines based on the formation of toxin-neutralizing antibody responses by immunization with the non-toxic binding subunits of bacterial exo-toxins (Cholera toxin, heat-labile toxin of *E. coli*) have been proposed (Jacob, C. O., et al., 1983, *Proc. Natl. Acad. Sci. U.S.A.* 80:7611; Jacob, C. O., et al., 1984, *EMBO J.* 3:2889).

The hepatitis B virion is a 42 nm enveloped structure containing a small DNA genome. The envelope proteins are encoded by the S gene (preS, $preS_2$ and S), one of the four open reading frames of the HBV genome (Tiollais, P. et al., 1985, *Nature* 317:489). These polypeptides contain the hepatitis B surface antigen (HBsAg). HBsAg particles derived from human plasma or similar HBsAg particles produced by recombinant DNA methods (some of which lack preS epitopes) have been shown to elicit a protective immune response and the purified particles represent current vaccines for HBV (Krugman, S., 1982, *J. Am. Med. Assoc.* 247:2012).

Flagellin

Flagella are organelles which are involved in locomotion of bacterial cells. The synthesis of structural proteins and the actual function of assembled flagella is a complex process involving the interactions of many genes and gene products (reviewed by Iino, T., 1977, *Ann. Rev. Genet.* 11:161). More than thirty-five genes have been defined which play a role in flagellar function in *E. coli*, and gene products for at least seventeen of these have been identified. The actual flagellar organelle is composed of three major structural elements, and spans from the cell cytoplasm, across the cell membranes, and culminates in a large extracellular domain. The filament is composed of a single subunit protein, flagellin, and is the major structural component of the organelle, accounting for more than 95% of the total mass.

The structural genes for flagellin have been termed H1 and H2 in Salmonella (Iino, T., 1969, *Bacteriol. Rev.* 33:454–475), H in *Bacillus subtilis* (Joys, T. M. and Frankel, R. W., 1967, *J. Bacteriol.* 94:32–37) and *Pseudomonas aeruginosa* (Iino, T., 1969, *Ann. Rep.* Natl. Inst. Genet. Jpn. 20:94), and hag in *E. coli* (Armstrong, J. B. and Adler, J., 1969, *J. Bacteriol.* 97:156–161). The basal body is the most complex part of the organelle and serves both to anchor the organelle to the cell and as part of the motor-like apparatus which rotates the filament. Finally, the hook serves to attach the filament to the basal body.

Rotation of the filament is responsible for flagella-mediated locomotion. Each filament consists of several thousand copies of the flagellin subunit resulting in a helical structure typically 5–10 u in length (for most *E. coli* and Salmonella species; MacNab, P., 1987, in *Eschericia coli* and *Salmonella typhimurium*, Neidhardt, F. C., Eds. American Society for Microbiology, Washington, D.C., pp. 70–83). Mutations in the flagellin structural gene have been observed to produce changes in efficiency of filament formation, filament shape, sensitivity to flagellotropic phage, and/or the antigenic specificity of the flagella (Yamaguchi, S. and Iino, T., 1969, *J. Gen. Microbiol.* 55:59–74; Iino, T., et al., 1974, *J. Gen. Microbiol.* 81:37–45; Horiguchi, T., et al., 1975, *J. Gen. Microbiol.* 91:139–149). Filaments are assembled extracellularly by sequential addition of flagellin monomers to the distal end of the growing filament, and the rate of elongation decreases inversely with the length of the filament until growth ceases, thus regulating filament length.

Flagella are found primarily, although not exclusively, on the surface of rod and spiral shaped bacteria, including members of the genera Escherichia, Salmonella, Proteus, Pseudomonas, Bacillus, Campylobacter, Vibrio, Treponema, Legionella, Clostridia, Caulobacter, and others. These flagella, although they perform the same function, are polymorphic in molecular weight across genera, ranging from 28–66 kd. A high degree of antigenic polymorphism is seen even within a single genus, such as Salmonella, and is useful for identifying individual serotypes within a single species (Edwards, P. R. and Ewing, W. H., 1972, *Identification of Enterobacteriaceae*, 3d ed., Burgess Publishing Co., Minneapolis, Minn.). Structural analyses of several bacterial flagella have revealed a common architecture among filaments isolated from different bacteria (Wei, L.-N. and Joys, T. M., 1985, *J. Mol. Bio.* 186:791; DeLange, R. J., et al., 1976, *J. Biol. Chem.* 251:705; Gill, P. R. and Agabian, J., *Biol. Chem.* 258:7395). Most striking is a high degree of protein sequence homology at the amino and carboxy termini of these molecules, and the presence of a polymorphic central region which is responsible for the antigenic diversity among different flagella.

Host immune responses to antigens on the surface of bacteria have been well documented (Horowitz, S. A. et al., 1987, *Infect. Immun.* 55:1314; Naito, Y., et al., 1987, *Infect. Immun.* 55:832; Zhang, Y. X., et al., 1987, *J. Immunol.* 138:575; Norgard, M. V., 1986, *Infect. Immun.* 54:500; Nagy, L. K., 1985, *Vet. Rec.* 117:408; Levine, M. M., et al., 1984, *Infect. Immun.* 44:409; Zak, K., et al., 1984, *J. Infect. Dis.* 149:166). Flagella, and especially flagellar filaments, have been shown to be potent immunogens under conditions of natural infection and artificial immunization, and in some cases, the response to antigenic determinants present on flagella have been shown to be protective (Young, R. J., et al., 1979, *Infect. Immun.* 25:220; Eubanks, E. R., et al., 1976, *Infect. Immun.* 15:533; Smith, H. L., Jr., 1974, *App. Micro.* 27:375; Dwyer, J. M. and Mackay, I. R., 1972, *Int. Arch.*

Allergy Appl. Imm. 43:434; Ebersole, J. L. and Molinari, J. A., 1976, Infect. Immun. 13:53; Ebersole, J. L., et al., 1975, Infect. Immun. 12:353; Stevenson, J. R. and Stronger, K. A., 1980, Am. J. Vet. Res. 41:650; Tamura, Y., et al., 1984, Micro. Imm. 28:1325). Kuwajima (1988, J. Bact. 170:485) has described the production of E. coli mutants with altered flagella antigenicity by the introduction of deletions into the central region of the flagellin hag gene.

U.S. Pat. No. 4,702,911 discloses the use of purified subunits of bacterial pili, hairlike organelles attached to the outer bacterial surface, in vaccine formulations.

International PCT Publication No. WO 87/02385, published Apr. 23, 1987, discloses the expression of a proinsulin sequence and a beta-lactamase sequence as fusion proteins with the B. subtilis flagellin hag gene.

SUMMARY OF THE INVENTION

The present invention is directed to recombinant genes and their encoded proteins which are recombinant flagellin fusion proteins. Such proteins comprise an epitope encoded by a functional flagellin structural gene and at lease one epitope of a heterologous organism, which epitope is immunogenic upon introduction of the fusion protein into a vertebrate host. These epitopes are recognized by B cell and/or T cell epitopes. The epitope of a heterologous organism can be inserted into a region which is non-essential to function of the encoded flagellin, yet does not destroy its function, such as the hypervariable region of the flagellin structural gene. In a particularly preferred embodiment, the epitope of a heterologous organism is inserted between the natural EcoRV sites of the Salmonella H1-d gene. The recombinant flagellin proteins of the invention are exported to the cell surface, where, in a preferred embodiment, they assemble into functional flagella containing the heterologous epitope. In other embodiments, the recombinant flagellin fusion proteins of the invention can provoke a cellular, a mucosal, or a humoral response.

The recombinant flagellin genes and proteins can be formulated for use as vaccines for protection against infection by the heterologous organism. They can also provide protection against conditions or disorders caused by an antigen of the heterologous organism. Expression as a recombinant flagellin fusion protein according to the present invention provides a method for presenting any desired epitope in an immunogenic form, to stimulate immune responses, including humoral, mucosal and/or cell-mediated immune responses. In a specific embodiment, the recombinant flagellin genes of the invention can be expressed by attenuated invasive bacteria, in live oral vaccine formulations. In another specific embodiment, the recombinant flagellin fusion proteins can be formulated for use in subunit vaccines.

In specific embodiments of the invention detailed in the examples section, epitopes of malaria circumsporozoite antigens, the B subunit of Cholera toxin, surface and presurface antigens of Hepatitis B, VP7 polypeptide of rotavirus, envelope glycoprotein of HIV, and M protein of Streptococcus are expressed on recombinant flagellin fusion proteins which assemble into functional flagella, and which provoke an immune response directed against the heterologous epitope, in a vertebrate host.

| Definitions | |
|---|---|
| bp | = base pairs |
| CRM197 | = mutant diphtheria toxin molecule |
| CS | = circumsporozoite |
| CT-B | = Cholera toxin B subunit |
| CTP3 | = A peptide representing amino acid residue numbers 50 to 64 of the B subunit of Cholera toxin (Jacob, C. O., et al., 1984, Proc. Natl. Acad. Sci. U.S.A. 81:7893) |
| DPAPPNAN | = Peptide (asp-pro-ala-pro-pro-asn-ala-asn) representing the immunodominant consensus repeating epitope of Plasmodium berghei circumsporozoite protein |
| DTT | = dithiothreitol |
| ELISA | = enzyme-linked immunosorbent assay |
| HBsAg | = the surface antigen of Hepatitis B |
| HIV | = Human Immunodeficiency virus |
| kd | = kilodaltons |
| KLH | = keyhole limpet hemocyanin |
| Mab | = monoclonal antibody |
| NANP | = Peptide (asn-ala-asn-pro) representing the immunodominant repeating epitope of Plasmodium falciparum circumsporozoite protein |
| PAGE | = polyacrylamide gel electrophoresis |
| PBS | = phosphate-buffered saline |
| RSV | = respiratory syncytial virus |
| VP7 | = a major outer shell polypeptide of rotavirus |

DESCRIPTION OF THE FIGURES

FIG. 2A. Schematic representation of the H1-d flagellin protein. Hypervariable region IV is denoted by cross-hatching. The locations of EcoRV restriction sites in the corresponding gene sequence are indicated.

FIGS. 2B–2D. Nucleotide and deduced amino acid sequence of the H1-d flagellin gene (from : Wei, L. N. and Joys, T. M., 1985, J. Mol. Biol. 186:791). The EcoRV restriction sites are underlined.

FIG. 3A. Nucleotide and deduced amino acid sequence of synthetic oligonucleotides encoding three full and two half copies of the P. falciparum circumsporozoite immunodominant repeating epitope (NANP).

FIG. 3B. Nucleotide and deduced amino acid sequence of synthetic oligonucleotides encoding two copies of the P. berghei circumsporozoite immunodominant consensus repeating epitope (DPAPPNAN).

FIG. 4A. Schematic representation of the Cholera toxin B subunit protein illustrating the location of the CTP3 epitope.

FIG. 4B. Nucleotide and deduced amino acid sequences of synthetic oligonucleotides encoding the CTP3 epitope of the Cholera toxin B subunit. Annealed oligonucleotides were treated with Klenow enzyme in order to create flush ends prior to ligation into the plasmid vector, as described in Example 1.

FIG. 6A–6D. Western Blot analysis of recombinant flagellins expressed in attenuated Salmonella. Cell extracts were electrophoresed and transferred to nitrocellulose filters as described in Example 1. The antibody probes used to detect recombinant flagellin molecules were: FIG. 6A: rabbit anti-H1-d antiserum; FIG. 6B: anti-*P. berghei* circumsporozoite Mab 3.28; FIG. 6C: anti-*P. falciparum* circumsporozoite Mab 4D9; FIG. 6D: rabbit anti-Cholera toxin amino acid residues 50–64 (CTP3 peptide) peptide serum. Plasmid constructions and host strains are indicated above each lane.

FIG. 10 shows amino acid and synthetic oligonucleotide sequences of HBsAg (ayw) S 122–137 and preS$_2$ 120–145, and map of the flagellin gene. The blackened region represents the hypervariable region. H is HindIII; R is EcoRV; P is PstI and K is KpnI.

DETAILED DESCRIPTION OF THE INVENTION

Figure 1:
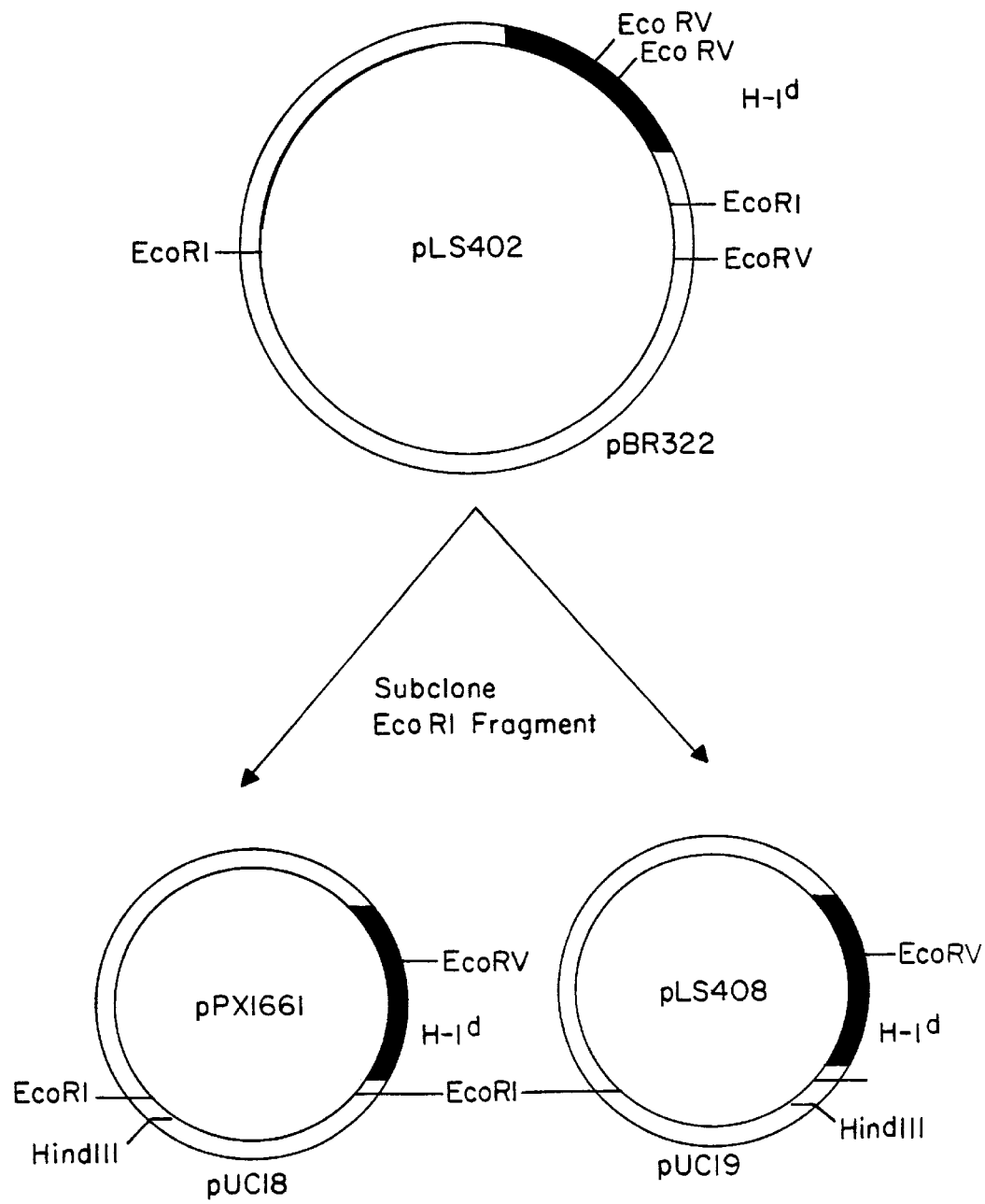
FIG. 1. Diagrammatic representation of plasmids pLS402, pPX1651, and pLS408, encoding the H1-d flagellin structural gene. Plasmid pLS402 was isolated from a genomic library of Salmonella muenchen DNA constructed in pBR322 (Wei, L.-N. and Joys, T. M., 1985, J. Mol. Biol. 186:791). The coding region for the H1-d flagellin gene (darkened area) is present in a 3.8 kb EcoRI genomic fragment, and contains two EcoRV restriction sites. An additional EcoRV site is present on the vector. The two subclones, plasmids pPX1651 and pLS408, were constructed by first inserting the 3.8 kb genomic fragment of pLS402 into the EcoRI site of pUC18 and pUC19, respectively, resulting in constructions pPX1650 and pLS405, respectively. The 51 bp EcoRV fragment was then deleted from each of these plasmids, resulting in plasmids pPX1651 and pLS408, each of which now had a unique EcoRV restriction site available for insertion of oligonucleotides specifying a foreign epitope.
Figure 5:
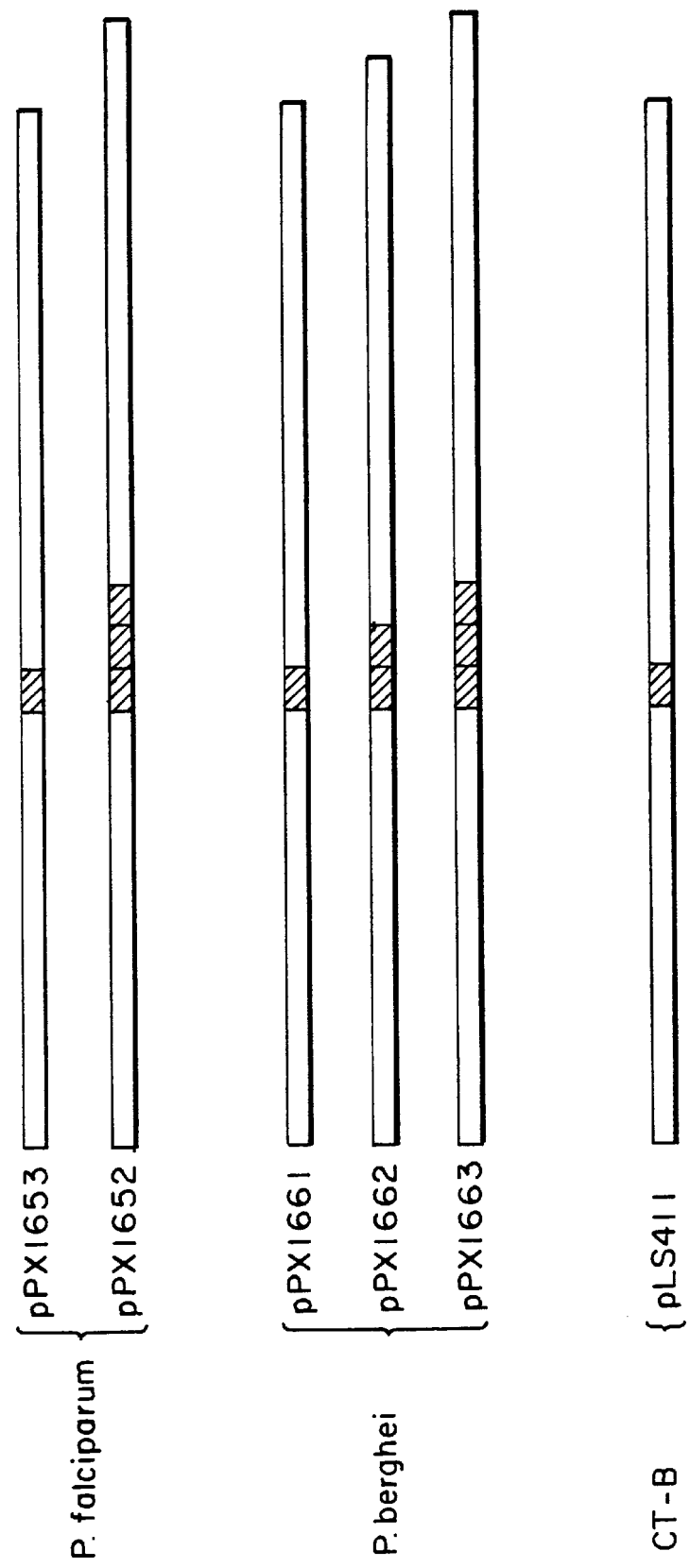
FIG. 5. Schematic representation of the recombinant flagellin fusion proteins, constructed as described in Example 1. Cross-hatched areas represent the heterologous sequences, from the CS proteins of *P. falciparum* or *P. berghei*, or the B subunit or Cholera toxin (CT-B), as indicated.

The present invention relates to recombinant flagellin structural genes which are expressed as recombinant flagellin fusion proteins. Such recombinant genes comprise a sequence encoding an epitope specified by a flagellin structural gene and a sequence encoding an epitope of a heterologous organism, which epitope is immunogenic upon introduction of the fusion protein into a vertebrate host. The epitope of a heterologous organism can be inserted into a region which is non-essential to function of the encoded flagellin. However, such insert should not destroy flagellar function. In a preferred embodiment, the epitope of a heterologous organism can be inserted into the hypervariable region of the flagellin structural gene (e.g., between the natural EcoRV sites of the Salmonella H1-d gene).

The invention also relates to the fusion flagellin proteins encoded by such genes, and the uses of these genes and proteins in vaccine formulations, for protection against infection by the heterologous organism or for protection against conditions or disorders caused by an antigen of the organism. Expression as a recombinant flagellin fusion protein according to the present invention provides a method for presenting any desired epitope in an immunogenic form, to stimulate immune responses (including humoral, mucosal and/or cell-mediated immune responses). In a specific embodiment, the recombinant flagellin genes of the invention can be expressed by attenuated invasive bacteria, in a live vaccine formulation. In another specific embodiment, the recombinant flagellin fusion proteins can be formulated for use in subunit vaccines.

In specific embodiments of the invention detailed in the examples sections below, epitopes of malaria circumsporozoite antigens, the B subunit of Cholera toxin, surface and presurface antigens of Hepatitis B, VP7 polypeptide antigens of rotavirus, envelope glycoprotein of HIV, and M protein of *Streptococcus pyogenes*, are expressed on recombinant flagellin fusion proteins which assemble into functional flagella, and which provoke an immune response directed against the heterologous epitope, in a vertebrate host.

The method of the invention may be divided into the following general stages solely for the purpose of description:

a. isolation of the flagellin gene;

b. isolation of sequences encoding immunogenic epitopes for expression as recombinant flagellins;

c. construction of recombinant flagellin genes;

d. expression in bacterial hosts;

e. determination of immunopotency of the heterologous epitope(s) expressed as a recombinant flagellin; and f. formulation of a vaccine.

The invention further pertains to a method of eliciting an immune response (including humoral, mucosal and/or cell-mediated immune responses) by administering to a vertebrate host, a bacterium transfected to express a recombinant flagellin fusion protein of this invention in a physiologically acceptable carrier. Preferably, the bacterium is live and infectious but cannot cause significant disease in the vertebrate host. Alternatively, the recombinant flagellar fusion protein itself can be administered to the host to elicit an immune response.

Anti-fungal vaccines can be used to prevent mycoses, these include, but are not limited to the fungi listed in Table I. (Braude et al., (1986), *Infectious Diseases and Medical Microbiology*; Feigin et al., (1987), *Textbook of Pediatric Infectious Diseases* 35; Mandell et al., (1985), *Principles and Practice of Infectious Diseases*, Section F.) Other uses for vaccines include eliciting anti-hormone responses for such purposes as enhanced contraception, enhanced feed conversion and hormone imbalance. Further uses include anti-cancer therapy and prophylaxis, anti-allergy therapy and production of immune prophylactic and immunotherapeutic agents.

Isolation of the Flagellin Gene

Any flagellin structural gene can be used for the construction of a recombinant gene encoding a fusion flagellin protein containing a heterologous epitope. Such flagellin genes include but are not limited to the H1 and H2 genes of Salmonella, H of *Bacillus subtilis* and *Pseudomonas aeruginosa*, and hag of *E. coli*.

Several of the flagellin genes have been cloned and sequenced (see, e.g., Kuwajima, G., et al. 1986, *J. Bact.* 168:1479; Wei, L.-N. and Joys, T. M., 1985, *J. Mol Biol.* 186:791–803; and Gill, P. R. and Agabian, N., 1983, *J. Biol. Chem.* 258:7395–7401; incorporated by reference herein).

If the cloned flagellin gene is not readily available, it may be cloned by standard procedures known in the art (see, e.g., Maniatis, T., et al., 1982, *Molecular Cloning, A Laboratory Manual*, Cold Spring Harbor Laboratory, Cold Spring Harbor, New York), with any flagellated bacterial cell potentially serving as the nucleic acid source for the molecular cloning. Such bacteria include but are not limited to Escherichia, Salmonella, Proteus, Pseudomonas, Bacillus, Campylobacter, Vibrio, Treponema, Legionella, Clostridia, and Caulobacter.

Nucleotide sequence analysis of the cloned gene can be carried out by various procedures known in the art, e.g., the method of Maxam and Gilbert (1980, *Meth. Enzymol.* 65:499–560), the Sanger dideoxy method (Sanger, F., et al., 1977, *Proc. Natl. Acad. Sci. U.S.A.* 74:5463), or use of an automated DNA sequenator (e.g., Applied Biosystems, Foster City, Calif.).

Isolation of Sequences Encoding Immunogenic Epitopes for Expression as Recombinant Flagellins Any DNA sequence which encodes an epitope of a heterologous organism, which when expressed as a flagellin fusion protein, produces protective immunity against such organism or against a condition or disorder caused by an antigen, can be isolated for use in the vaccine formulations of the present invention. In a preferred embodiment, such an organism is a pathogenic microorganism. For example, such a heterologous epitope may be found on bacteria, parasites, viruses or fungi which are the causative agents of diseases or disorders. In addition, epitopes of allergens and cancer cells can be used. Such bacteria, parasites, viruses or fungi include but are not limited to those listed in Table I.

TABLE I

HETEROLOGOUS ORGANISMS FROM WHICH DNA CAN BE ISOLATED FOR CONSTRUCTION OF GENES ENCODING FLAGELLIN FUSION PROTEINS

PARASITES:

Plasmodium spp.
Eimeria spp.
Schistosoma spp.
Trypanosoma spp.
Babesia spp.
Leishmania spp.
Cryptosporidia spp.
Toxoplasma spp.
Pneumocystis spp.

BACTERIA:

*Vibrio cholerae*
*Streptococcus pyogenes*
*Neisseria menigitidis*
*Neisseria gonorrhoeae*
*Corynebacteria diphtheriae*
*Clostridium tetani*
*Branhamella catarrhalis*
*Bordetella pertussis*
Haemophilus spp. (e.g., *influenzae*)
Chlamydia spp.
Enterotoxigenic *Escherichia coli*

VIRUSES:

Human Immunodeficiency virus, type I
Human Immunodeficiency virus, type II
Simian Immunodeficiency virus
Human T lymphocyte virus, type I, II and III
Respiratory syncytial virus
Hepatitis A virus
Hepatitis B virus
Hepatitis C virus
Non-A, Non-B Hepatitis Virus
Herpes simplex virus, type I
Herpes simplex virus, type II
Cytomegalovirus
Influenza virus
Parainfluenza virus
Poliovirus
Rotavirus
Coronavirus
Rubella virus
Measles virus
Mumps virus
Varicella
Epstein Barr virus
Adenovirus
Papilloma virus
Yellow Fever virus

FUNGI:

Candida spp. (especially *albicans*)
Cryptococcus spp. (especially *neoformans*)
Blastomyces spp. (*dermatitidis*)
Histoplasma spp. (especially *capsulatum*)
Coccidioides spp. (especially *immitis*)
Paracoccidioides spp. (especially *brasiliensis*)
Aspergillus spp.

In another embodiment, an epitope of an antigen of a nematode can be expressed as a fusion protein, to protect against disorders caused by such worms.

Potentially useful antigens for vaccine formulations can be identified by various criteria, such as the antigen's involvement in neutralization of a pathogen's infectivity (Norrby, E., 1985, Summary, in *Vaccines* 85, Lerner, R. A., R. M. Chanock, and F. Brown (eds.), Cold Spring Harbor Laboratory, Cold Spring Harbor, N.Y., pp. 388–389), type or group specificity, recognition by patients' antisera or immune cells, and/or the demonstration of protective effects of antisera or immune cells specific for the antigen. In addition, the antigen's encoded epitope should preferably display a small or no degree of antigenic variation in time or amongst different isolates of the same pathogen.

In a preferred embodiment, the heterologous sequence encodes an immunopotent dominant epitope of a pathogen. In addition, molecules which are haptens (i.e., antigenic, but not immunogenic) may also be expressed as recombinant flagellin, since the flagellin may function as a carrier molecule in conferring immunogenicity on the hapten. Recombinant flagellins containing epitopes which are reactive with antibody although incapable of eliciting immune responses, still have potential uses in immunoassays.

Peptides or proteins which are known to contain antigenic determinants can be incorporated into recombinant flagellins. If specific antigens are unknown, identification and characterization of immunoreactive sequences should be carried out. One way in which to accomplish this is through the use of monoclonal antibodies generated to the surface or other molecules of a pathogen. The peptide sequences capable of being recognized by the antibodies are defined epitopes. Alternatively, small synthetic peptides conjugated to carrier molecules can be tested for generation of monoclonal antibodies that bind to the sites corresponding to the peptide, on the intact molecule (see, e.g., Wilson, I. A., et al., 1984, *Cell* 37:767). Other methods known in the art which may be employed for the identification and characterization of antigenic determinants are also within the scope of the invention.

In a specific embodiment, any DNA sequence which encodes a Plasmodium epitope, which when expressed as a flagellin fusion protein, is immunogenic in a vertebrate host, can be isolated for use according to the present invention. The species of Plasmodium which can serve as DNA sources include but are not limited to the human malaria parasites *P. falciparum, P. malariae, P. ovale, P. vivax*, and the animal malaria parasites *P. berghei, P. yoelii, P. knowlesi*, and *P. cynomolgi*. The antigens or fragments thereof which can be expressed as flagellin fusion proteins are antigens which are expressed by the malaria parasite at any of the various stages in its life cycle, such as the sporozoite, exoerythrocytic (development in hepatic parenchymal cells), asexual erythrocytic, or sexual (e.g., gametes, zygotes, ookinetes) stages. In a particular embodiment, the heterologous epitope to be expressed is an epitope of the circumsporozoite (CS) protein of a species of Plasmodium (see Example 1). Analogous CS proteins have been identified on the surfaces of sporozoites of all species of Plasmodium tested. Circumsporozoite protein antigens expressed in attenuated Salmonella spp. can be used as live vaccines directed against sporozoites, the invasive form of malaria parasites transmitted by the female Anopheles mosquito. Any epitope of a region of the CS protein important in the induction of protective humoral or cell-mediated immune response can be used in the vaccine formulations of the present invention. (See, e.g., Dame, J. B., et al., 1984, *Science* 225:593; Arnot, D. D., et al., 1985, *Science* 230:815; Weber et al., 1987, *Exp. Parasitol.* 63:295; Enea, V., et al., 1984, *Science* 225:628; Enea, V., et al., 1984, *Proc. Natl. Acad. Sci. U.S.A.* 81:7520; Godson, G. N. et al., 1983, *Nature* 305:29; and McCutchan, T. F., et al., 1985, *Science* 230:1381 which references are incorporated by reference herein). For example, in one embodiment, the peptide asn-ala-asn-pro, representing the *P. falciparum* CS immunodominant repeating epitope, can be expressed by the recombinant bacteria of the invention. In another embodiment, the peptide asp-pro-ala-pro-pro-asn-ala-asn, representing the *P. berghei* CS protein immunodominant repeating epitope, can be expressed.

In another specific embodiment, the Th2R epitope (Good, M. F., et al., 1987, *Science* 235:1059) of the *P. falciparum* CS protein can expressed as a recombinant flagellin protein in the vaccine formulations of the present invention.

In yet another embodiment, the heterologous epitope to be expressed as a recombinant flagellin fusion protein comprises a peptide of the B subunit of Cholera toxin. Suitable peptides are described by Jacob et al. As described by Jacob et al., (1983, *Proc. Natl. Acad. Sci. U.S.A.* 80:7611) peptides corresponding to several regions of the B subunit of cholera toxin have been synthesized and coupled to an immunogenic carrier in an effort to define epitopes which induce neutralizing antibodies. When these conjugates were used to raise antibodies in rabbits, one of these, encoding amino acids 50–64 (peptide CTP3), was shown to induce antibodies which recognized the native toxin and neutralized the biochemical (adenylate cyclase activation) and biological (intestinal fluid secretion) effects of the intact holotoxin (Jacob, C. O. et al., 1984, *Proc. Natl. Acad. Sci. U.S.A.* 81:7893).

Other epitopes which can be expressed as flagellin fusion proteins include but are not limited to the following: epitopes of the G protein of respiratory syncytial virus (RSV) (Collins et al., 1984, *Proc. Natl. Acad. Sci. U.S.A.* 81:7683); neutralizing epitopes on Poliovirus I VP1 (Emini, E., et al., 1983, *Nature* 304:699); neutralizing epitopes on envelope glycoproteins of HIV I (Putney, S. D., et al., 1986, *Science* 234:1392–1395); epitopes present on Hepatitis B surface antigen (Itoh, Y., et al., 1986, *Nature* 308:19; Neurath., A. R., et al., 1986, *Vaccine* 4:34); epitopes of Diphtheria toxin (Audibert, F., et al., 1981, *Nature* 289:543); streptococcus 24M epitope (Beachey, E. H., 1985, *Adv. Exp. Med. Biol.* 185:193); and epitopes on gonococcal pilin (Rothbard, J. B. and Schoolnik, G. K., 1985, *Adv. Exp. Med. Biol.* 185:247).

The flagellin fusion proteins in the vaccine formulations of the invention can also comprise an epitope of a heterologous organism, which when the fusion protein is introduced into a vertebrate host, induces an immune response that protects against a condition or disorder caused by an antigen containing the epitope. For example, in this embodiment of the invention, flagellin fusion proteins which encode an epitope of snake venom, bee venom, a hormone, sperm (for contraception), an allergy-inducing antigen or any other antigen to which an immune response is desired, may be used. In one particular embodiment, an epitope of an antigen of fat cell membranes can be expressed as a recombinant flagellin protein for formulation of a vaccine to decrease fat content in animals used as food sources. In another embodiment, a tumor-specific antigen can be expressed as a recombinant flagellin fusion protein, for induction of a protective immune response against cancer. In yet another embodiment, an epitope of a bacterial enterotoxin may also be expressed as a flagellin fusion protein. The nucleotide and deduced amino acid sequences for several bacterial enterotoxins have been determined (Mekalanos, J. J., et al., 1983 *Nature* 306:551; Leong, J., et al., 1985, *Infect. Immun.* 48:73).

In another embodiment of the invention, DNA sequences encoding large regions of proteins which contain several B cell epitopes (i.e., epitopes capable of inducing a humoral immune response) and T cell epitopes (i.e., epitopes capable of inducing a cell-mediated immune response) can be introduced into the flagellin gene for expression as flagellin fusion proteins. By providing natural T helper cell epitopes as well as antibody-inducing epitopes, one can thus prime recipients for boosting by contact with a pathogenic heterologous organism.

The gene sequences encoding the heterologous epitope to be expressed as a recombinant flagellin according to the present invention, can be isolated by techniques known in the art including but not limited to purification from genomic DNA of the microorganism, by cDNA synthesis from RNA of the microorganism, by recombinant DNA methods (Maniatis, T, et al., 1982, *Molecular Cloning, A Laboratory Manual*, Cold Spring Harbor Laboratory, Cold Spring Harbor, N.Y.), or by chemical synthesis.

Construction of Recombinant Flagellin Genes

In the construction of a recombinant flagellin gene of the present invention, sequences of a flagellin gene have sequences inserted into them or are replaced by a sequence (s) encoding an epitope(s) of a heterologous organism.

First, the domains of the flagellin gene which are desired to have sequences inserted into them or are replaced by the heterologous sequences should be identified. Those flagellin sequences which are necessary and sufficient for transport of the flagellin protein to the distal end of the flagellum (or of the hook for initiation of a new flagellar filament) are desired to be conserved. This conservation results in a recombinant flagellin molecule which retains the ability to be expressed on the surface of the cell, as flagellar filament, thus facilitating isolation and purification of these recombinant molecules for use as components of a subunit vaccine, or facilitating their presentation to the immune system, in a live vaccine embodiment.

Structural analysis of several bacterial flagella have revealed a common architecture among filaments isolated from different bacteria (Wei, L.-N. and Joys, T. M., 1985, *J. Mol. Biol.* 186:791–803; DeLange, R. J., et al., 1976, *J. Biol. Chem.* 251:705; Gill, P. R., and Agabian, N., 1983, *J. Biol. Chem.* 258:7395). Most striking is a high degree of protein sequence homology at the amino and carboxy termini of these filaments (suggesting that these regions are required for structural integrity and/or function) and the presence of a polymorphic central region which is responsible for the antigenic diversity among different flagella (id.;

see also, Iino, T., 1977, *Ann. Rev. Genet.* 11:161–182, and references cited therein). Structural restraints on this hypervariable central region are inconspicuous since isolates have been identified which differ in both number of amino acid residues as well as primary sequence.

In a preferred embodiment, a DNA sequence encoding a heterologous epitope is inserted into, or replaces, the central hypervariable region of the flagellin monomer. This embodiment allows the construction of recombinant flagellin monomers which may retain the ability to form intact flagella. The ability to assemble into flagella would, in the context of a live vaccine formulation, result in the presentation of a high concentration of the heterologous epitope, which exists on each flagellin monomer, to the immune system of the in vivo host. Presentation as an organized polymeric structure would afford a much stronger antigenic stimulus than the same material as monomer. Also, upon expression by a bacterium, presence of flagella on the external surface of the bacteria would allow a more effective presentation of the heterologous epitope. Furthermore, assembly into intact flagella would facilitate purification of the recombinant flagellin molecules, since various procedures for such purification are known in the art and may be used. In a most preferred embodiment, the recombinant flagellin molecules expressed by a parental nonmotile strain of bacteria produce functional flagella yielding motile bacteria which may thus more effectively present the heterologous epitope to the host immune system than a nonmotile strain, by virtue of the foreign epitope's presence on the external surface of the bacteria, and possibly the relatively greater invasiveness afforded by their motility.

As described in the examples sections below, we have been able to introduce DNA encoding epitopes of heterologous organisms into the central hypervariable region of the flagellin gene of *Salmonella muenchen* without adversely affecting flagellar externalization and assembly.

Many strategies known in the art can be used in the construction of the recombinant flagellin gene. For example, the relevant sequences of the flagellin gene and of the heterologous gene can, by techniques known in the art, be cleaved at appropriate sites with restriction endonuclease(s), isolated, and ligated. If cohesive termini are generated by restriction endonuclease digestion, no further modification of DNA before ligation may be needed. If however, cohesive termini of the DNA are not available for generation by restriction endonuclease digestion, or different sites other than those available are preferred, any of numerous techniques known in the art may be used to accomplish ligation of the heterologous DNA at the desired sites. For example, cleavage with a restriction enzyme can be followed by modification to create blunt ends by digesting back or filling in single-stranded DNA termini before ligation. Alternatively, the cleaved ends of the flagellin gene or heterologous DNA can be "chewed back" using a nuclease such as nuclease Bal 31, exonuclease III, lambda exonuclease, mung bean nuclease, or T4 DNA polymerase exonuclease activity, to name but a few, in order to remove portions of the sequence. An oligonucleotide sequence (a linker) which encodes one or more restriction sites can be inserted in a region of the flagellin gene by ligation to DNA termini. The subsequent ligation of a heterologous gene sequence into the cloning restriction site, so that both sequences are in the correct translational reading frame uninterrupted by translational stop signals, will result in a construct that directs the production of a flagellin fusion protein. A linker may also be used to generate suitable restriction sites in the heterologous gene sequence. Additionally, flagellin or heterologous gene sequences can be mutated in vitro or in vivo in order to form new restriction endonuclease sites or destroy pre-existing ones, to facilitate in vitro ligation procedures. Any technique for mutagenesis known in the art can be used, including but not limited to, in vitro site-directed mutagenesis (Hutchinson, C., et al., 1978, *J. Biol. Chem.* 253:6551), use of TAB™ linkers (Pharmacia), etc.

The particular strategy for constructing gene fusions will depend on the specific flagellin sequence to be replaced or inserted into, as well as the heterologous gene to be inserted.

The recombinant flagellin gene should be constructed in or transferred into a vector which is capable of replication and expression in a bacterial host. In a preferred embodiment, the recombinant flagellin gene may also be inserted into the bacterial chromosomal DNA. One way in which this may be accomplished is by recombinational exchange with a plasmid-borne recombinant flagellin gene. In an alternative embodiment, the recombinant flagellin gene can be inserted into a cloning vector which can exist episomally, e.g., a plasmid or bacteriophage, which is then used to transform or infect appropriate host bacterial cells, where the recombinant DNA is replicated and expressed.

The transformation of bacterial hosts with the DNA molecules that incorporate the recombinant flagellin gene enables generation of multiple copies of the flagellin sequence. A variety of vector systems may be utilized for expression within the bacterial host, including but not limited to plasmids such as pUC plasmids and derivatives, pBR322 plasmid and derivatives, bacteriophage such as lambda and its derivatives, and cosmids. In a specific embodiment, plasmid cloning vectors which can be used include derivatives of ColE1 type replicons (for additional information, see Oka et al., 1979, *Mol. Gen. Genet.* 172:151–159). The ColE1 plasmids are stably maintained in *E. coli* and *Salmonella typhimurium* strains as monomeric molecules with a copy number of about 15–20 copies per cell.

Various regulatory expression elements can be used, which are any of a number of suitable transcription and translation elements that are active in bacteria. For instance, promoters which may be used to direct the expression of the recombinant flagellin sequence include but are not limited to the lactose operon promoter of *E. coli*, the hybrid trp-lac UV-5 promoter (tac) (DeBoer, H., et al., 1982, in *Promoter Structure and Function*, Rodriguez, R. L. and Chamberlain, M. J., eds., Praeger Publishing, New York), the leftward ($P_L$) and the rightward ($P_R$) promoters of bacteriophage lambda, the bacteriophage T7 promoter, the trp operon promoter, the lpp promoter (the *E. coli* lipoprotein gene promoter; Nakamura, K. and Inouye, I., 1979, *Cell* 18:1109–1117), etc. Other promoters produced by recombinant DNA or synthetic techniques may also be used to provide for transcription of the inserted sequences. Alternatively, the native flagellin promoter may be used.

Specific initiation signals are also required for efficient translation of inserted protein coding sequences. These signals include the ATG initiation codon and adjacent sequences. In cases where the native flagellin gene sequences encoding its own initiation codon and adjacent sequences are inserted into the appropriate expression vectors, no additional translational control signals may be needed. However, in cases where the native flagellin translational signals are not present, exogenous translational control singals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Methods for constructing the appropriate expression vectors may include in vitro recombinant DNA and synthetic techniques and in vivo recombinants (genetic recombination).

For reviews on maximizing gene expression, see Roberts and Lauer, 1979, *Meth. Enzymol.* 68:473; and Reznikoff, W. and Gold, M., 1986, *Maximizing Gene Expression*, Plenum Press, New York.

U.S. Pat. No. 4,237,224 to Cohen and Boyer describes production of recombinant plasmids using processes of cleavage with restriction enzymes and joining with DNA ligase by known methods of ligation. These recombinant plasmids are then introduced by means of transformation or electrophoration and replicated in unicellular cultures including procaryotic organisms and eucaryotic cells grown in tissue culture.

Another method for introducing recombinant DNA molecules into unicellular organisms is described by Collins and Hohn in U.S. Pat. No. 4,304,863. This method utilizes a packaging/tranduction system with bacteriophage vectors (cosmids).

Expression in Bacterial Hosts

The expression vector comprising the recombinant flagellin sequence should then be transferred into a bacterial host cell where it can replicate and be expressed. This can be accomplished by any of numberous methods known in the art including but not limited to transformation (e.g., of isolated plasmid DNA into the attenuated bacterial host), phage tranduction (Schmeiger, 1972, *Mol. Gen. Genetics* 119:75), conjugated between bacterial host species, electroporation, etc.

In a specific embodiment, any attenuated bacterial hosts which express the recombinant flagellin can be formulated as live vaccines. Such bacteria include but are not limited to attenuated invasive strains and attenuated Campylobacter, Shigella or Escherichia species.

Expression in Attenuated Invasive Bacteria

In a preferred embodiment of the present invention, the expression vector comprising the recombinant flagellin sequence is transferred into an attenuated invasive bacteria, where it is expressed, thus producing a bacterial strain suitable for use as a live vaccine.

Any of various attenuated invasive bacteria can be used as a vehicle to express the recombinant flagellin so that its heterologous epitope is effectively presented to the host immune system, in the vaccine formulations of the present invention. The vaccine bacteria retain their invasive properties, but lose in large part their virulence properties, thus allowing them to multiply in the host to a limited extent, but not enough to cause significant disease or disorder. Examples of invasive bacteria which, in attenuated forms, may be used in the vaccine formulations of the invention include but are not limited to Salmonella spp., invasive *E. coli* (EIEC), and Shigella spp. In a preferred embodiment, invasive bacteria which reside in lymphoid tissues such as the spleen (e.g., Salmonella spp.) are used. Such bacteria can invade gut epithelial tissue and/or Peyer's patches, disseminate throughout the reticuloendothelial system, and gain access to mesenteric lymphoid tissue, liver, and spleen, where they multiply or at least survive for a time, and induce humoral and cell-mediated immunity.

Attenuated invasive bacteria may be obtained by numerous methods including but not limited to chemical mutagenesis, genetic insertion, deletion (Miller, J., 1972, *Experiments in Molecular Genetics*, Cold Spring Harbor Laboratory, Cold Spring Harbor, N.Y.) or recombination using recombinant DNA methodology (Maniatis, T., et al., 1982, *Molecular Cloning, A Laboratory Manual*, Cold Spring Harbor Laboratory, Cold Spring Harbor, N.Y.), laboratory selection of natural mutations, etc. Methods for obtaining attenuated Salmonella strains which are non-reverting non-virulent auxotrophic mutants suitable for use as live vaccines are described in U.S. Pat. No. 4,735,801 issued on Apr. 5, 1988 and copending U.S. patent application Ser. No. 798,052, filed Nov. 14, 1985, by Stocker, which are incorporated by reference herein in their entirety. A reliable method to achieve attenuation of Salmonella has been described (Hoiseth, S. K., and Stocker, B. A. D., 1981, *Nature* 291:238; Stocker B. A. D., et al., 1982, *Develop. Biol. Standard* 53:47; and U.S. Pat. No. 4,550,081) and can be used in a particular embodiment of the invention.

Attenuated Salmonella which can be used in the live vaccine formulations of the invention include but are not limited to those species listed in Table II.

TABLE II

SALMONELLA SPECIES WHICH, IN ATTENUATED FORMS, CAN BE USED IN THE VACCINE FORMULATIONS OF THE PRESENT INVENTION*

*S. typhi*
*S. typhimurium*

TABLE II-continued

SALMONELLA SPECIES WHICH, IN ATTENUATED
FORMS, CAN BE USED IN THE VACCINE
FORMULATIONS OF THE PRESENT INVENTION*

S. paratyphi A
S. paratyphi B
S. enteritidis
(e.g., serotype dublin)

*For a complete description of Salmonella serotypes, see Edwards and Ewing, 1986, Classification of the Enterobacteriaceae, 4th ed., Elsevier, N.Y.

In specific embodiments, Salmonella bacteria that have been attenuated by chromosomal deletion of gene(s) for aromatic compound biosynthesis (aro), or mutation in the galE gene, or that are cya⁻, crp⁻ vir plasmid⁻, etc., can be used. Aro mutants which can be used include but are not limited to S. typhi strains 543Ty and 541Ty, for use in vaccines for humans, and S. typhimurium SL3261 and SL1479, and S. enteriditis serotype dublin SL1438, (also termed S. dublin) for use in animals. (See U.S. Pat. No. 4,550,081 for a description of S. typhimurium strain SL1479 and S. dublin strain SL1438). S. typhi strains such as 543Ty and 541Ty are avirulent in humans by virute of attenuation by deletion affecting genes aroA and/or purA (Levine, M. M., et al., 1987, J. Clin. Invest. 79:888). Mutants of S. dublin, such as SL1438, and of S. typhimurium, such as SL3261, can be used in the development of animal model systems, since these species are capable of causing animal diseases equivalent to typhoid fever. galE mutants which can be used include but are not limited to Salmonella typhi strains Ty21a (Germanier, 1984, Bacteria Vaccines, Academic Press, NY pp. 137–165) Salmonella typhimurium G30D, etc.

In a preferred embodiment, a plasmid expression vector containing a recombinant flagellin gene can be isolated and characterized in E. coli, before transfer to an attenuated Salmonella stain, e.g., by phage transduction (Schmeiger, 1972, Mol. Gen. Genetics 119:75), because of the high transformation frequencies of E. coli K12 relative to those of Salmonella such as S. typhimurium.

Determination of Immunopotency of the Heterologous Epitope(s) Expressed as a Recombinant Flagellin Immunopotency of the heterologous epitope expressed as a recombinant flagellin, in its live vaccine formulation, can be determined by monitoring the immune response of test animals following immunization with bacteria expressing the recombinant flagellin. In a subunit vaccine formulation, the immune response of test animals can be monitored following immunization with the isolated recombinant flagellin molecule, as flagellar filaments or monomer, which can be formulated with an appropriate adjuvant to enhance the immunological response. Suitable adjuvants include, but are not limited to, mineral gels, e, aluminum hydroxide, surface active substances such as lysolecithin, pluronic polyols, polyanions, peptides, oil emulsions, and potentially useful human adjuvants such as BCG (Bacille Calmette-Guerin) and Corynebacterium parvum. Test animals may include mice, guinea pigs, rabbits, chickens, chimpanzees and other primates, and eventually human subjects. Methods of introduction of the immunogen may include oral, intradermal, intramuscular, intraperitoneal, intravenous, subcutaneous, intranasal or any other standard routes of immunizations.

The immune response of the test subjects can be analyzed by various approaches such as: (a) the reactivity of the resultant immune serum to the native antigen or a fragment thereof containing the heterologous epitope, or to the isolated naturally occurring heterologous organism, as assayed by known techniques, e.g., enzyme linked immunosorbant assay (ELISA), immunoblots, radioimmunoprecipitations, etc., (b) the reactivity of lymphocytes isolated from the immunized subject to the native antigen or fragment thereof, or the heterologous organism, as assayed by known techniques, e.g., blastogenic response assays, cytotoxicity assays, delayed type hypersensitivity, etc., (c) the ability of the immune serum to neutralize infectivity of the organism in vitro or the biologic activity of the native antigen, and (d) protection from disease and/or mitigation of infectious symptoms in immunized animals.

Formulation of a Vaccine

In this embodiment of the invention, the recombinant flagellins which comprise an epitope of a heterologous organism are formulated for vaccine use. Such vaccines formulations can comprise live vaccines or subunit vaccine formulations. The vaccine formulations of the invention are of use in both animals and humans.

Live Bacteria as Vaccines

The purpose of this embodiment of the invention is to formulate a vaccine in which the immunogen is an attenuated invasive bacterial strain that expresses a recombinant flagellin comprising an epitope of a heterologous organism so as to elicit an immune (humoral and/or cell-mediated) response to the heterologous epitope that will protect against infections by the organism or conditions or disorders caused by an antigen of the organism. The bacteria of the vaccine comprise strains that are infectious for the host to be vaccinated. In a preferred embodiment, such strains are attenuated invasive bacteria such as Salmonella species. Other suitable species can include but are not limited to Shigella and E. coli. In a most preferred embodiment, the recombinant flagellin genes are expressed by the host bacteria as flagellin monomers that assemble into functional flagella, allowing the heterologous epitope on the recombinant molecules to be presented in a large number of copies to the host immune system.

The live vaccine formulation can be univalent or multivalent. Multivalent vaccines can be prepared from a single or few recombinant bacteria which express one or more heterologous epitopes, which may be of different organisms. A single bacterium can express more than one epitope of the same or different antigens. The various epitopes may be expressed within the same recombinant flagellin protein, on separate recombinant flagellin molecules encoded by the same or different expression vectors, or in different bacteria.

Many methods may be used to introduce the live vaccine formulations of the invention; these include but are not limited to oral, intradermal, intramuscular, intraperitoneal, intravenous, subcutaneous, transcutaneous, and intranasal routes, including the natural route of infection of the parent wild-type bacterial strain. In an embodiment in which an oral vaccine formulation is for animal use, vaccination of livestock can be accomplished by employing the live vaccine formulation as a supplement to feed or in drinking water.

In specific embodiments, attenuated Salmonella expressing a recombinant flagellin comprising an epitopes of a malarial circumsporozoite protein, the B subunit of cholera toxin, surface and presurface antigens of Hepatitis B, VP7 polypeptide of rotavirus, envelope glycoprotein of HIV, and M protein of Streptococcus can be formulated as vaccines.

A preferred embodiment of the invention is the use of an avirulent non-pathogenic Salmonella oral vector delivery system. Use of this system can not only preclude some of the potential side-effects associated with the use of other delivery vehicles such as vaccinia virus and adenovirus, but can also provide for convenient oral administration of vaccines. Furthermore, it can be expected that oral vaccination will induce a mucosal as well as a systemic immune response, thereby increasing the immunogenic potential of the vaccine.

Subunit Vaccines

The heterologous peptide expressed as a recombinant flagellin fusion protein, may be used as an immunogen in subunit vaccine formulations, which may be multivalent. The multivalent vaccine formulation can comprise recombinant flagella, or a recombinant flagellin monomer containing more than one heterologous epitope, which epitope may be of different organisms, or several flagellin molecules, each encoding a different heterologous epitope, etc.

The recombinant flagellin gene product may be purified for purposes of vaccine formulation from any vector/host systems that express the heterologous protein, such as transduced or transformed bacteria. For example, bacterial flagellar filaments are easily removed from the intact bacterium by mechanical means which do not otherwise damage the cell, thus allowing them to be easily purified without introducing harsh, denaturing agents. Standard procedures known in the art can be used for the purification of recombinant flagellin, either as monomers or as (assembled) flagella (see e.g., Gill, P. R., and Agablan, N., 1983, *J. Biol. Chem.* 258:7395–7401; Weissborn, A., et al., 1982, *J. Biol. Chem.* 257:2066–2074; Gill, P. R., and Agabian, N., 1982, *J. Bacteriol.* 150:925–933; Lagenaur, C., and Agabian, N., 1976, *J. Bacteriol.* 128:435–444; Fukuda, A., et al., 1978, *FEBS Lett.* 95:70–75; Stevenson, J. R., and Stonger, K. A., 1980, *Am. J. Vet. Res.* 41(4):650–653).

Furthermore, isolated flagella samples can be solubilized (e.g., by dissociation upon exposure either to pH 3 or to pH 11 at low ionic strength; DeLange, R. J., et al., 1976, *J. Biol. Chem.* 251(3):705–711) to flagellin subunits and then reassociated to flagella by known procedures (eg, Weissborn, A., et al., 1982, *J. Biol. Chem.* 257:2066–2074) in order to: (a) aid in the purification of the recombinant flagellins by removing undesirable contaminants; and/or (b) produce an immunogen for multivalent vaccine formulation, by association of recombinant flagellin monomers encoding different heterologous epitopes.

The purified protein(s) should be adjusted to an appropriate concentration, formulated with any suitable vaccine adjuvant and packaged for use. Suitable adjuvants include, but are not limited to: mineral gels, e.g., aluminum hydroxide; surface active substances such as lysolecithin, pluronic polyols; polyanions; peptides; oil emulsions; and potentially useful human adjuvants such as BCG (Bacille Calmette-Guerin) and *Cornebacterium parvum*. The immunogen may also be incorporated into liposomes, or conjugated to polysaccharides and/or other polymers for use in a vaccine formulation.

In instances where the recombinant flagellin gene product is a hapten, i.e., a molecule that is antigenic in that it can react selectively with cognate antibodies, but not immunogenic in that it cannot elicit an immune response, the hapten may covalently bound to a carrier or immunogenic molecule; for instance, a large protein such as serum albumin will confer immunogenicity to the hapten coupled to it. The hapten-carrier may be formulated for use as a vaccine.

Many methods may be used to introduce the vaccine formulations described above; these include, but are not limited to, oral, intradermal, intramuscular, intraperitoneal, intravenous, subcutaneous and intranasal routes.

Uses of Antibodies Directed Against Recombinant Flagellin

The antibodies generated against heterologous organisms by immunization with the recombinant flagellin of the present invention also have potential uses in diagnostic immunoassays, passive immunotherapy, and generation of antiidiotypic antibodies.

The generated antibodies may be isolated by standard techniques known in the art (e.g., immunoaffinity chromatography, centrifugation, precipitation, etc.) and used in diagnostic immunoassays to detect the presence of viruses, bacteria, or parasites of medical or veterinary importance in human or animal tissues, blood, serum, etc. The antibodies may also be used to monitor treatment and/or disease progression. Any immunoassay system known in the art, such as those listed herein, may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The vaccine formulations of the present invention can also be used to produce antibodies for use in passive immunotherapy, in which short-term protection of a host is achieved by the administration of pre-formed antibody directed against a heterologous organism.

The antibodies generated by the vaccine formulations of the present invention can also be used in the production of antiidiotypic antibody. The antiidiotypic antibody can then in turn be used for immunization, in order to produce subpopulation of antibodies that bind the initial antigen of the pathogenic microorganism (Jerne, N. K., 1974, *Ann. Immunol.* (Paris) 125c:373; Jerne, N. K., et al., 1982, *EMBO* 1:234).

Immunoassays

The recombinant flagellin gene products of the present invention, or fragment thereof, expressing foreign epitope (s), may be used as antigens in immunoassays for the detection of antibodies to the epitope(s). The heterologous protein, or fragments thereof, may also be used to detect the same or related epitope(s) by competition assays. The recombinant flagellin products, or the foreign epitope(s) expressed by them, may be used in any immunoassay system known in the art including but not limited to competitive and noncompetitive assay systems using techniques such as radioimmunoassays, ELISA (enzyme-linked immunosorbent assay), "sandwich" immunoassay, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

EXAMPLE 1

Construction of Flagellin Minus Vaccine Strains

The two live-vaccine strains used as hosts of flagellin-specifying plasmids are SL5927 and SL5928. Each was obtained from an aromatic-dependent *S. dublin* parent strain which was wild-type in respect of flagellar characteristics, that is motile and with the single flagellin gene, H1-g,p, determining the phase-1 flagallar antigen, g,p, characterics of the monophasic species, *S. dublin*.

SL5927 was obtained from SL1437, an aromatic-dependent live vaccine strain whose construction is described in U.S. Pat. Nos. 4,735,801 and 4,550,081, the teachings of which are incorporated herein by reference.

SL5928 was obtained from another aromatic-dependent live vaccine strain of S. dublin, SL5631, whose construction is described below.

Each motile strain was used as recipient in transduction, with SL5669, which is an S. typhimurium strain with transposon Tn10 inserted in gene H1-i, for its phase-1 flagellar antigen, i. Selection was made for clones which were resistant to tetracycline, because of replacement of gene H1-g,p of the recipient by gene H1-i::Tn10 of the donor. A tetracycline resistant clone, found nonmotile (because of replacement of the wild-type flagellin gene by the gene inactivated by the transposon) and free of the phage, P22 HT105/1 used to effect the transduction, was retained, SL5927 from the cross with SL1438 as recipient and SL5928 from that with SL5631 as recipient.

SL5631 is a stable aromatic-dependent derivative of a virulent S. dublin strain, SVA47. It was obtained by two steps of transduction, by the method used to construct aroA (deletion) strains of S. typhi (Edwards, M. F., 1985, Ph.D. Thesis, Stanford University, California).

Expression of Heterologous Epitopes as Recombinant Flagellin Fusion Proteins

The construction and expression of recombinant flagellin genes encoding foreign epitopes important in the induction and expression of protective immune responses is described. The heterologous parasitic and bacterial epitopes which were expressed as recombinant flagellin were of the malarial CS protein, and of the B subunit of cholera toxin. The recombinant flagellin molecules were introduced into and expressed by attenuated Salmonella strains, which can be used in live vaccine formulations.

Materials and Methods Plasmids and Bacterial Strains

The bacterial strains used were Salmonella strains SL1438 (ATCC Accession No. 39184) and SL5927 (ATCC Accession No. 67944), and E. coli strain CL447. Plasmid pLS402 contains a 3.8 kb EcoRI fragment of genomic DNA encoding the complete H1-d flagellin structural gene from S. muenchen inserted into the EcoRI site of plasmid pBR322 (Wei, L.-N. and Joys, T. M., 1985, J. Mol. Biol. 186:791). Plasmid pUC18, pUC19, and E. coli strain JM103 were obtained from Bethesda Research Laboratories (BRL; Bethesda, Md.).

Conditions for Restriction Enzyme Digestion

Restriction endonucleases BamHI, ClaI, EcoRI and EcoRV were purchased from Bethesda Research Laboratories (BRL, Bethesda, Md.). Digestions were carried out by suspending DNA in the appropriate restriction buffer, adding 2–3 units of enzyme per microgram of DNA, and incubating at 37° C. overnight.

Restriction buffer used for BamHI digestions consisted of 10 mM Tris-HCl (pH 7.5), 10 mM $MgCl_2$, and 100 mM NaCl.

Restriction buffer used for EcoRI and ClaI digestions consisted of 10 mM Tris-HCl (pH 7.5), 10 mM $MgCl_2$, and 50 mM NaCl.

Restriction buffer used for EcoRV digestions consisted of 10 mM Tris-HCl (pH 7.5), 10 mM $MgCl_2$, and 150 mM NaCl.

Creation of Flush Ends in DNA Fragments

To create blunt ends for ligation, DNA termini with 5' overhangs were filled out by the action of the large fragment of DNA polymerase I (Klenow fragment). For filling out with Klenow fragment, 1–25 micrograms of DNA were treated with 1 unit per microgram DNA of Klenow enzyme (BRL) in a 50 microliter reaction volume in buffer containing 66 mM Tris-HCl, pH 7.5, 6.6 mM $MgCl_2$, 1 mM dithiothreitol (DTT), and 20 nM of all four deoxynucleotide triphosphates (dATP, dCTP, dGTP, and TTP) for 30 minutes at room temperature.

Gel Purification of DNA Fragments

After restriction enzyme digestions, DNA fragments of varying sizes were separated by polyacrylamide gel electrophoresis using TBE buffer (0.089 M Tris, 0.089 M boric acid, 0.002 M EDTA, pH 7.5) at 15 volts/cm. Acrylamide gels were cast by diluting a stock solution of acrylamide-:bisacrylamide (40:1.1) to either 6% or 8% with TBE buffer depending on the size of the DNA fragment to be isolated. Following vertical electrophoresis, bands were visualized by ethidium bromide fluorescence, and the appropriate band was excised and placed in dialysis tubing containing a 1:10 dilution of TBE buffer. This was placed in a chamber containing the same buffer and electroeluted at 100 milliamps for 2 hours. The electroeluted DNA fragment was recovered by removing the liquid contents from the bag and precipitating the DNA with 2 volumes of cold ethanol in the presence of 300 mM sodium acetate.

Synthesis and Purification of Oligonucleotides

Oligonucleotides were synthesized on the 0.2 micromole scale, on an Applied Biosystems Inc. model 380B DNA synthesizer, using beta-cyanoethyl-phosphoramidite chemisty (Sinha, N. D., et al., 1984, Nucl. Acids. Res. 12:4539–4544).

Oligonucleotides were purified by electrophoresis in a 0.4 mm thick 8% polyacrylamide gel in TBE buffer (0.01 M Tris-borate, pH 8.2, 1 mM EDTA), run at approximately 1600 volts with a constant power of 75 watts. Oligonucleotide bands were visualized by negative shadowing over a PEI (polyethylene-imine) thin-layer chromatography plate under ultraviolet light, and the band of full length product was excised from the gel. The synthetic oligonucleotide was eluted in 0.3 M sodium acetate pH 5.5, and was precipitated by the addition of two volumes of 100% ethanol, chilled to −20° C., and centrifuged at 14,000×g. The pellets were dried under vacuum and dissolved in TE buffer (10 mM Tris-HCl, pH 7.4, 1 mM EDTA).

Phosphate groups were incorporated at the 5' terminus of the synthetic oligonucleotides using T4 polynucleotides kinase (New England Biolabs, Beverly, Mass.). One microgram amounts of purified oligonucleotide were dissolved in 25 microliters of kinase buffer consisting of 70 mM Tris-HCl (pH 7.6), 10 mM $MgCl_2$, 5 mM DTT, with 1 mM adenosine triphosphate (ATP). This solution was incubated with 20 units of T4 polynucleotide kinase for 30 minutes at 37° C.

Annealing of complementary strands was achieved by mixing the kinased strands and heating to 60° C. for 1 hour and cooling to room temperature.

DNA Ligation

All ligations were accomplished using T4 DNA ligase purchased from BRL (Bethesda, Md.). Vector DNA and the appropriately treated isolated restriction fragment, or synthetic oligonucleotides, were resuspended in 30 microliters of ligase buffer (66 mM Tris-HCl, pH 7.5, 6.6 mM $MgCl_2$, 10 mM DTT, and 1 mM ATP), and 2 Weiss units of T4 DNA ligase enzyme was added. The ligation reaction was allowed to proceed for 18–24 hours at 4° C. Normally, 50–100 ng of vector DNA was ligated to approximately a 10-fold molar excess of insert DNA.

Transformation of Plasmid DNA

Plasmid constructions resulting from the ligation of synthetic oligonucleotides into plasmids pPX1651 or pLS408 were inserted into common laboratory strains of Escherichia coli by transformation techniques (for details, see Maniatis et al., 1982, Molecular Cloning, A Laboratory Manual, Cold Spring Harbor Laboratory, Cold Spring Harbor, N.Y.). Plasmid constructions were isolated and characterized first in *E. coli*, before transferring to Salmonella spp, because of the high transformation frequencies of *E. coli* K-12 relative to those of *S. typhimurium*. Plasmids were transferred into *S. typhimurium* LT-2 LB5010, a strain which is restriction-negative (but modification-proficient) for the three restriction systems of *Salmonella typhimurium*, and also contains a mutation in galE resulting in higher transformation frequencies (for a description of restriction systems of *Salmonella typhimurium*, see Bullas et al., 1980, *J. Bacteriol.* 141:275).

Plasmids were then inserted into attenuated Salmonella by transduction techniques. LB5010 containing the desired plasmid was grown in Luria broth (LB) to a density of $3 \times 10^8$ cells/ml, at which point D-galactose (to a final concentration of 1%) was added to the growth medium to induce synthesis of "smooth" lipopolysaccharide (LPS). Following 1.5 hours of growth in the presence of D-galactose, bacteriophage P22 HT 105/1 int was added to the culture to a multiplicity of infection of one. Following adsorption of the phage, cells were immobilized in LB containing 0.7% agar. Phage were harvested and used to transduce plasmids into any attenuated Salmonella containing LPS appropriate as receptor for the transducing phage P22.

Restriction Enzyme Analysis of DNA

Recombinant plasmid DNA was analyzed by digestion of DNA with appropriate restriction endonucleases and electrophoresis through 1% agarose gels run in TBE buffer containing 5 ug/ml ethidium bromide. Bands were detected by ethidium bromide fluorescence.

Polyacrylamide Gel Electrophoresis

To analyze recombinant flagellin proteins by sodium dodecyl sulfate (SDS)-polyacrylamide gel electrophoresis (PAGE), 500 microliters of an overnight culture of bacteria containing a recombinant plasmid were centrifuged, and the pellet was resuspended in 200 microliters of protein running mix (0.125 M Tris-HCl, pH 6.8, 2.5% SDS, 5% 2-mercaptoethanol, 10% glycerol, 0.005% bromophenol blue), and heated to 100° C. for 10 minutes. 20 microliters of each samples were electrophoresed under conditions described by Laemmli (Laemmli, U. K., 1979, *Nature* 227:680), through a stacking gel of 4% acrylamide and a separating gel of 10% acrylamide.

Western Blot Analysis

Following SDS-PAGE of protein samples, electrophoresed proteins were transferred to nitrocellulose sheets (Schleicher and Schuell, Keene, N.H.) by the method of Towbin et al., (Towbin, H., et al., 1979, *Proc. Natl. Acad. Sci. U.S.A.* 76:4350). After transfer, filters were blocked by incubation in phophate-buffered saline (PBS) with 0.5% Tween 20 for 15 minutes at room temperature. Primary antibodies were diluted to an appropriate concentration in PBS with 0.1% Tween 20 (PBS-Tween) and added to filters. Incubations were at room temperature for a period of at least one hour and as long as overnight. Filters were then washed in several changes of PBS-Tween, and horseradish peroxidase-conjugated *S. aureus* Protein A (Kirkegaard and Perry, Md.), at a concentration of 1 ug per milliliter, was added, followed by incubation for one hour at room temperature. Filters were then washed several times in PBS-Tween and the signal was developed with PBS containing 0.01% hydrogen peroxide, 0.06% 4-chloro-1-napthol (Sigma Chemical Co., St. Louis, Mo.) at room temperature until an appropriate signal was detected. This reaction was stopped by washing the filter several times with distilled water.

Enzyme-Linked Immunosorbent Assay for Serum Anti-Circumsporozoite Protein Antibodies To measure serum antibodies, 96 well polystyrene plates (NUNC) were coated with 5 ug/ml of DPAPPNANDPAPPNAN(KLH), a synthetic peptide representing two repeat units of *Plasmodium berghei* CS protein coupled to KLH by glutaraldehyde cross-linking. Each well received 0.1 ml of antigen in 0.1 M carbonate/bicarbonate buffer (pH 9.6). Plates were incubated at 37° C. in a humidified incubator for 18 hours, before being washed 3 times with PBS containing 0.05% Tween 20 (PBS-T) and blocked with 0.1% gelatin in PBS for 60 minutes at room temperature. Plates were washed 3 times with PBS-T, and serial dilutions for sera were added and incubated for 90 minutes at room temerperature. Anti-*P. berghei* CS Mab 3.28 was used as a positive control in assays. Plates were washed as before, and pre-optimized concentrations of alkaline phosphatase-conjugated goat anti-mouse immunoglobulin (at a 1:5000 serum dilution) were added to appropriate wells and incubated for 60 minutes at room temperature. Plates were washed again, and 100 microliters of substrate solution (p-nitrophenyl phosphate at 1 mg/ml in diethanolamine buffer, pH 9.6) was added to each well. The signals were developed for 60 minutes at room temperature, and read in a Bio-Tek automatic ELISA reader using dual wavelengths at 410 nm and 690 nm, blanking on air.

Partial Purification of Recombinant Flagella

Overnight cultures of *S. dublin* SL1438 harboring recombinant plasmids were used to inoculate 150 mm petri dishes containing 1.5% (w/v) Difco agar in LB medium supplemented with 100 ug/ml ampicillin, and plates were incubated for 48 hours at 37° C. These plates were then flooded with deionized water, and bacteria were gently removed from the surface by scraping. This suspension was blended at high speed in a standard food blender, and bacterial debris was removed by centriguation at 10,000 rpm in a Sorvall SS34 rotor for 30 minutes. Flagella present in the supernate were concentrated by ultracentrifugation at 50,000 rpm in a Beckman 70.1Ti rotor for one hour. These preparations of flagella were judged to be approximately 90% pure by Coomassie blue protein staining of SDS-PAGE gels, and protein concentrations were estimated by comparison with known amounts of standard proteins run on the same gels.

Immunization of Experimental Animals

Female C57BL/6 mice, approximately 6 weeks old (Jackson Laboratories, Bar Harbor, Me.) were immunized subcutaneously with approximately 25 micrograms of partially purified preparations for flagella emulsified in complete Freund's adjuvant. Four weeks later, mice were boosted subcutaneously with 25 micrograms of the same preparation of flagella emulsified in incomplete Freund's adjuvant. All animals were bled from the tail vein prior to the primary immunization, just before boosting, and two weeks after the boost.

For immunization with live, attenuated Salmonella, cultures of *S. dublin* SL1438 harboring recombinant plasmids were grown in LB medium supplemented with 100 ug/ml ampicillin to mid-log phase, harvested by centrifugation, washed with PBS, and resuspended to a concentration of $1 \times 10^8$ cells per ml. 0.1 ml of this suspension was administered intraperitoneally to 6 weeks old C57BL/6 mice (Jackson Laboratories, Bar Harbor, Me.). Four weeks later, animals were boosted with $1 \times 10^8$ cells prepared and administered in the same manner. Animals were bled as described above.

Assay for Bacterial Motility

*S. dublin* SL5927 is a non-flagellate (and thus non-motile) bacterial strain due to tranductional replacement of its only flagellin gene by H1-i::Tn10. The construction of SL5927 is described above in the section entitled "Construction of Flagellin Minus Vaccine Strains".

Overnight cultures of *S. dublin* SL5927 harboring recombinant plasmids were used to inoculate plates of motility agar (LB plus 100 ug/ml ampicillin with 0.3% w/v Difco agar) with the aid of an inoculating needle. Plates were incubated overnight at room temperature and for 6 hours at 37° C. The diameter of the zone of bacterial spreading was then measured, as an indicator of bacterial motility.

Ressults

Construction of Recombinant Flagellin Genes

Plasmid pLS402 contains a 3.8 kb EcoRI fragment of genomic DNA which includes the complete H1-d (H1 antigen d) flagellin structural gene (Wei, L.-N and Joys, T. M., 1985, *J. Mol. Biol.* 186:791–803) (FIGS. 2A, 2B) from *S. muenchen* (American Type Culture Collection Accession No. 8388) inserted into the EcoRI site of plasmid pBR322 (FIG. 1; Wei, L.-N., and Joys, T. M., 1985, *J. Mol. Biol.* 186:791). Examination of the published base sequence of the coding region for this gene (FIG. 2B) revealed two EcoRV restruction sites separated by 48 bp at positions 619 and 667. By comparison with sequences derived from other H1 genes, the region of the gene containing these two restriction sites was demonstrated to be highly variable in both primary amino acid sequence and in the number of residues. We thus concluded that this region of the gene may be dispensable for flagella assembly and function, and would thus be an appropriate location for the insertion of DNA encoding foreign epitopes. In order to utilize this strategy, it was necessary to subclone the H1-d gene onto a plasmid vehicle which did not have any EcoRV restriction sites. Therefore, the 3.8 kb EcoRI fragment of pLS402 was isolated and subcloned into the EcoRI site of pUC18 and of pUC19, resulting in the construction of plasmids pPX1650 and pLS405, respectively. These latter vectors could then be used to exchange the authetic H1-d DNA between nucleotide numbers 619 and 667 (FIG. 2B) for synthetic or cloned DNA encoding a foreign epitope. In order to further facilitate the screening of recombinant plasmids, the 48 bp fragment between the EcoRV sites in each plasmid was deleted by digesting pPX1650 and pLS405 with EcoRV and religating each of the digested plasmids. Transformants were then screened for the loss of the 48 bp fragment; pPX1651 and pLS408 were thus obtained (FIG. 1). These plasmids retained only a single EcoRV site for insertion of foreign epitopes. In addition, it was now possible to distinguish, by size, a vector with an insertion of a 48 bp piece of foreign DNA from a vector which had simply religated to itself.

To test the ability of foreign epitopes to be expressed as genetic fusions with flagellin, several genetic constructions were made, as described infra.

Construction of a Recombinant Flagellin Gene Which Encodes an Epitope of a Malaria Parasite as a Flagellin Fusion Protein Recombinant flagellin genes were constructed which encoded epitopes of malaria parasite (genus Plasmodium) circumsporozoite proteins as flagellin fusion proteins.

Initially, two complementary 48-residue oligonucleotides were synthesized encoding four copies of the *P. falciparum* circumsporozoite protein four-amino-acid repeat sequence (FIG. 3A). The sequences of these nucleic acid fragments were such that, when annealed, complementary three base overhangs were created which allowed oligonucleotides to ligate to themselves only in a head to tail fashion, thus ensuring insertion of multiple oligonucleotides all in the same orientation. After the fragments were annealed, they were blunt-ended by treatment with DNA polymerase large fragment (Klenow enzyme), and ligated to pPX1651 which had been digested previously with EcoRV. Following transformation of *E. coli* strain JM103, ampicillin-resistant colonies were screened for the presence of recombinant plasmids by restruction site analysis of plasmid DNA. Two recombinants were identified: pPX1653 contains a single copy of the inserted oligonucleotide, and pPX1652 contains three inserted oligonucleotides. By DNA sequence analysis, the three oligonucleotide fragments present in pPX1652, which were filled in by treatment with the Klenow fragement of DNA polymerase I prior to ligation with pPX1651, were inserted in the same orientation. This procedure resulted in the insertion of an additional asparagine residue between the 16 amino acid blocks encoded by the oligonucleotide. Western blotting of cell extracts, utililizing monoclonal antibodies specific for the *P. falciparum* repeat region, demonstrated that these clones expressed immunoreactive proteins of an appropriate molecular weight for recombinant flagellin.

A similar strategy was employed to create recombinant flagellin molecules expressing the repeated eight amino acid sequence of the *P. berghei* CS protein (FIG. 3B). In this set of experiments, oligonucleotides were ligated together prior to treatment with Klenow enzyme in order to ensure the insertion of contiguous oligonucleotides, all in the same orientation and without intervening DNA sequences. Clones were obtained containing one, two or three copies of the specific oligonucleotide, and were named pPX1661, pPX1662, and pPX1663, respectively. Bacteria harboring these clones were found to express immunoreactive proteins of the appropriate molecular weight when screened by western analysis utilizing a *P. berghei* CS-specific monoclonal antibody.

Construction of a Recombinant Flagellin Gene Which Encodes an Epitope of Cholera Toxin B Subunit as a Flagellin Fusion Protein A similar strategy was employed for the expression, as a flagellin fusion protein, of an epitope of an exotoxin of the pathogenic bacterium *Vibrio cholerae*. For the construction of this recombinant, complementary oligonucleotides (FIG. 4B) encoding the epitope represented by the CTP3 peptide (FIG. 4A) of the Cholera toxin B subunit (Jacob, C. O., et al., 1983, *Proc. Natl. Acad. Sci. U.S.A*. 80:7611) were synthesized. The amino acid sequence encoded by the synthetic oligonucleotides was as follows:

(N)Val—Glu—Val—Pro—Gln—Ser—Gly—His—Ile—Asp—Ser—Gln—Lys—Lys—Ala(C)

and represents residue numbers 50 to 64 (FIG. 4B) of the B subunit. The complementary oligonuclotides were annealed and blunt-ended by treatment with Klenow enzyme. These fragments were then inserted into the EcoRV site of pLS408 and transformed into *E. coli* CL477. A plasmid containing a single insert was identified by restriction analysis, and was named pLS411. pLS411 was confirmed by DNA sequencing of the insert and by Western blot analysis to contain the insert in the desired orientation, since it expressed a molecule of the appropriate molecular weight, which was recognized by both anti-H1-d antiserum and monoclonal and rabbit polyclonal antisera raised to the CTP3 peptide.

Expression of Recombinant Flagellin Fusion Proteins

In order to express these recombinant flagellin molecules in an attenuated bacterial strain for use as live vaccines, all of the constructions described above (FIG. 5) were introduced into attenuated strains of *S. dublin* (SL1438 and SL5927) by phage tranduction (Schmeiger, 1972, *Mol. Gen. Genetics* 119:75). The method used to attenuate these strains has been described by Stocker and his coworkers (Hoiseth, S. K. and Stocker, B. A. D., 1981, *Nature* 291:238; Stocker, B. A. D., et al., 1982, *Dev. Biol. Std.* 53:47; U.S. Pat. No. 4,550,081). Specifically, deletions were introduced into the gene aroA, resulting in pleiotropic requirements for phenylalanine, tryptophan, tyrosine, the folic acid precursor p-aminobenzoic acid, and the enterochelin precursor, dihydroxybenzoic acid. p-aminobenzoic acid is absent from animal tissues, and members of the Enterobacteriaceae are unable to assimilate folic acid from animal tissues, resulting in their attenuation within an animal or human host. Western blot analysis was performed on extracts from each of these strains, and the synthesis of recombinant flagellins was demonstrated using both antibodies directed against flagellin epitopes (FIG. 6), indicating that these strains could be valuable as live vaccines to induce immune responses against the foreign epitopes inserted into the flagellin molecules.

Immunogold Labeling of Recombinant Flagellin

Exposure of the foreign epitope at the surface of the flagella was detected by gold immunolabeling of the flagella of Formalin-fixed bacteria, with MAb TE33 as the first antibody. Strain SL5676 harboring either plasmid pLS411, which has the complete CTP3 insert or plasmid pLS408, with the in vitro deletion but not the insert were labeled by treatment with MAb TE33 and gold-conjugated goat antibody to mouse IgG (Janssen) for electron microscope visualization (×30,000). Visualization of the label indicated that the CTP3 epitope was present on the surface of the bacteria.

Recombinant Flagellin Fusion Proteins are able to Assemble into Functional Flagella The ability of the recombinant flagellin proteins to polymerize into intact flagella and to therefore be present on the external surface of the bacteria was demonstrated by their restoration of motility in a normally non-motile (because flagellin-negative) host (Table III).

TABLE III

MOTILITY IN S. DUBLIN SL5927[1]

| Plasmid | Heterologous Antigen[2] | Diameter of Spread (mm)[3] |
|---|---|---|
| pPX1650* | — | 20 |
| pPX1651* | — | 22 |
| pPX1652* | P. falciparum CS protein | 13.5 |
| pPX1653* | P. falciparum CS protien | 18 |
| pPX1661* | P. berghei CS protein | 21 |
| pPX1662* | P. berghei CS protein | 13.5 |
| ppX1663* | P. berghei CD protein | 12 |
| pLS411 | cholera toxin B subunit | 4.5 |
| pUC18 | — | 0 |

[1](non-motile) S. dublin SL5927 = S. dublin SL1438 H1-i::Tn10
[2]The native antigen, a portion of which is expressed as a recombinant flagellin fusion protein encoded by the plasmid at left.
[3]Overnight cultures were stabbed into the center of 60 mm petri dishes containing 0.3% agar in LB medium supplemented with 100 ug/ml ampicillin. Plates were incubated for 16 hours at room temperature and for 6 hours at 37° C. The diameter of the zone of bacterial spread in millimeters was then measured.
*Encoding at least a portion of the flagellin H1-d gene.

SL5927 is a non-motile derivative of SL1438 constructed by interrupting the chromosomal copy of the structural gene encoding the H1 antigen (flagellin) by insertion of a transposable element (Tn10); this strain, like other S. dublin, has no H2 allele. SL5927 is constructed as described above in the section entitled "Construction of Flagellin Minus Vaccine Strains". Introduction of any of the recombinant flagellin plasmids restores at least partial motility to this strain (Table III), indicating that these recombinant flagellins can polymerize into functional flagella, and that the foreign epitopes are therefore present on the external surface of the cell.

Figure 7:
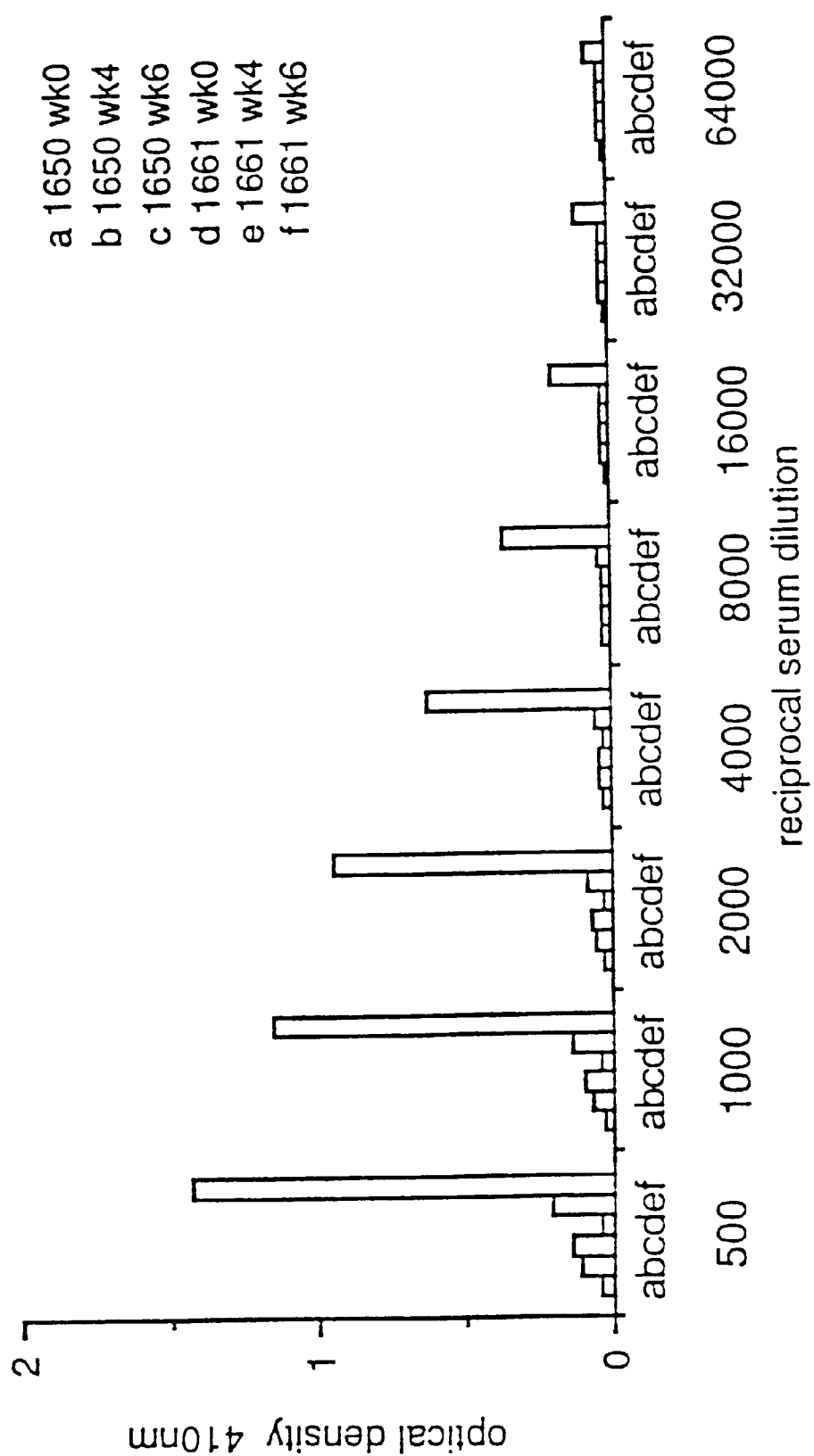
FIG. 7. Detection of antibody to malaria circumsporozoite (CS) epitope in mice immunized with recombinant flagellin proteins. Mice were immunized and boosted with partially purified wild-type H1-d flagella (encoded by plasmid pPX1650) or recombinant flagella containing two copies of the *P. berghei* CS immunodominant repeat (encoded by plasmid pPX1661). Serial dilutions of sera obtained from these animals at weeks 0, 4 and 6 post primary immunization were assayed by ELISA for binding to synthetic peptides consisting of two copies of the *P. berghei* CS repeat coupled to keyhole limpet hemocyanin (KLH). Data presented are mean values calculated from five individual animals per group. a: plasmid pPXI650, at week 0; b: plasmid pPX1650 at week 4; c: plasmid pPX1650 at week 6; d: plasmid pPX1661 at week 0; e: plasmid pPX1661 at week 4; f: plasmid pPX1661 at week 6.

Immunogenicity of the Heterologous Epitopes on Recombinant Flagellin Fusion Proteins In order to demonstrate the ability of recombinant flagellins to deliver foreign epitopes to the host immune system, C57BL/6 mice were immunized with partially purified flagella isolated from S. dublin SL1438 expressing in each flagellin molecule two copies of the P. berghei CS immunodominant repeat (encoded by plasmid pPX1661) or wild type H1-d flagella (encoded by plasmid pPX1650). Mice were injected subcutaneously with approximately 25 micrograms of flagellin protein emulsified in complete Freund's adjuvant at week 0 and boosted with 25 micrograms of the same preparation subcutaneously in incomplete Freund's adjuvant 4 weeks later. Animals were bled prior to the first and second immunizations and again two weeks after the booster. Sera were assayed by ELISA for antibodies specific for synthetic peptides encoding two copies of the P. berghei CS repeat (DPAPPNAN). Anti-P. berghei antibodies (FIG. 7) were slightly above background 4 weeks after the primary immunization, and levels increased dramatically following the booster imunization, whereas levels of these antibodies in animals immunized with control wildtype flagella (encoded by plasmid pPX1650) were not significantly different from prebleed values (FIG. 7, week 0).

Figure 8:
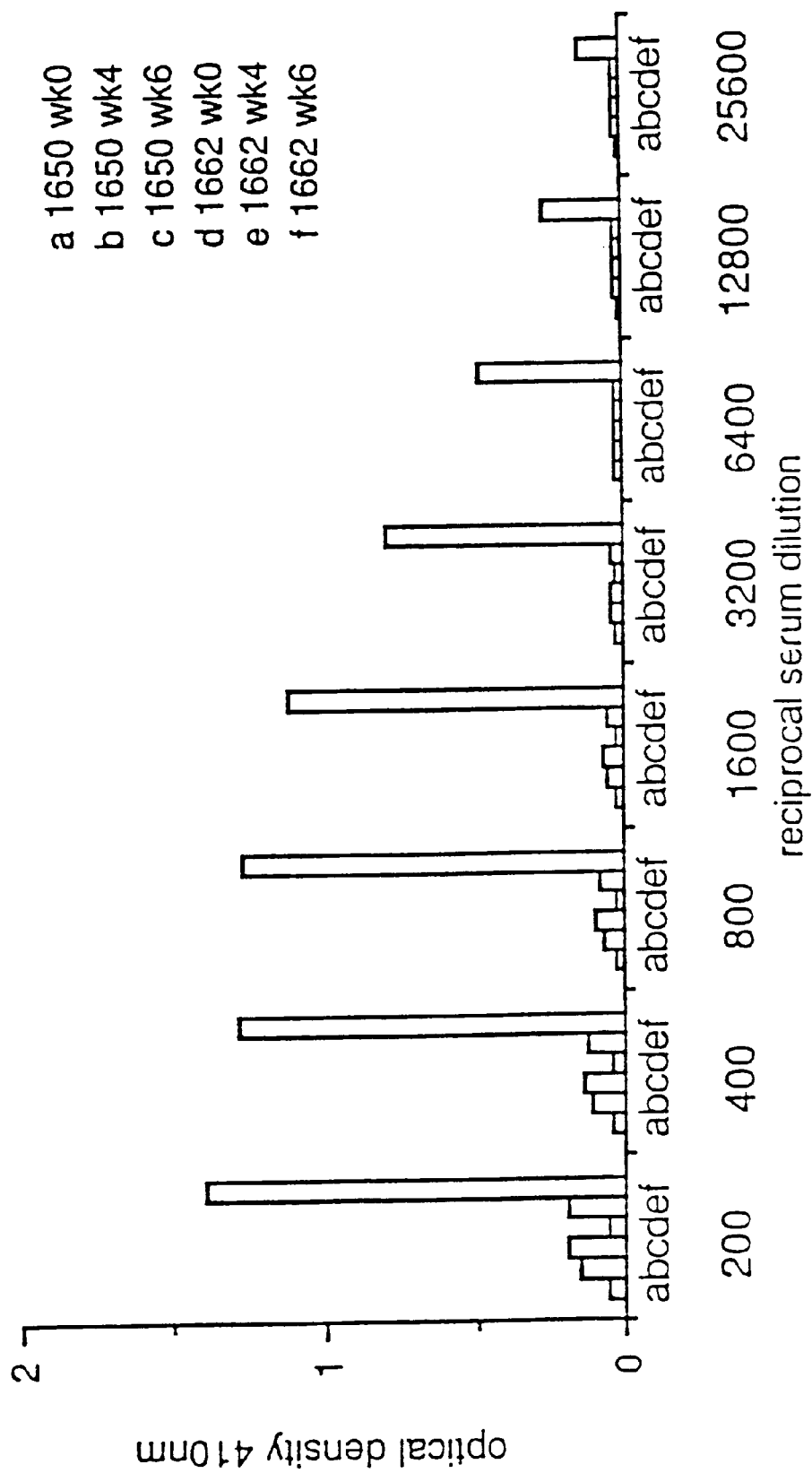
FIG. 8. Detection of antibody to malaria circumsporozoite (CS) epitope in mice immunized with live attenuated Salmonella expressing recombinant flagellin fusion proteins. Mice were immunized and boosted as described in Example 1. Serial dilutions of sera obtained from these animals at weeks 0, 4 and 6 post primary immunization were assayed by ELISA for binding to synthetic peptides consisting of two copies of the *P. berghei* CS repeat coupled to KLH. Data presented are mean values calculated from five individual animals per group, except for week 6, where only one animal remained per group. a: plasmid pPX1650, at week 0; b: plasmid pPX1650 at week 4; c: plasmid pPX1650 at week 6; d: plasmid pPX1662 at week 0; e: plasmid pPX1662 at week 4; f: plasmid pPX1662 at week 6.

Immunization of C57BL/6 mice with live S. dublin SL1438 expressing recombinant flagella carrying the P. berghei CS epitope (encoded by plasmid pPX1662) also induced significant levels of serum antibodies to this epitope relative to control animals immunized with the same bacterial strain expressing wild-type H1-d flagella (encoded by plasmid pPX1650) (FIG. 8), illustrating the ability of live attenuated bacteria to deliver a foreign epitope as a flagellin fusion protein expressed on the surface of these organisms.

Figure 9:
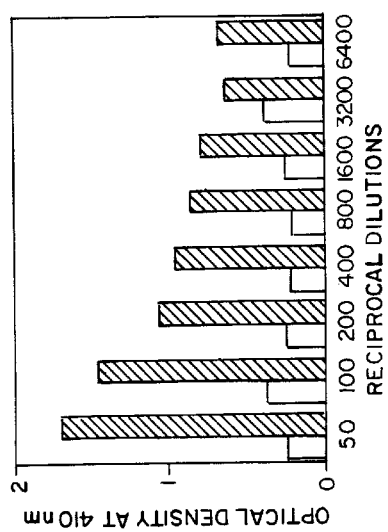
FIG. 9 shows a histogram of antibody responses of five mice immunized with SL5929, formalin killed *Salmonella dublin* vaccine expressing the CTP3 epitope of Cholera toxin B subunit.

For tests of immunogenicity, we replaced the phase-1 flagellin gene, H1-g,p of aromatic-dependent live-vaccine S. dublin strain SL1438 (Clements, J. et al., 1987, *Infect. Immunol.* 53:685; Dougan, G et al., 1987, *Parasite Immunol.* 9:151; and Poirier, T. P. et al., 1988, *J. Exp. Med.* 68:25) with a flagellin allele inactivated by a transposon, H1-i::Tn10; as S. dublin is monophasic, the resulting strain, SL5928, was nonmotile but became motile when transformed with plasmids containing either the wild-type, the deletion, or the chimeric form of H1-d, just as observed for the flagellin-negative S. typhimurium host, SL5676. The pUC-derived plasmids are stable in the live vaccine strain used, as shown by the ampicillin resistance of all of more than 100 colonies from a bacterial suspension after two passages in broth without ampicillin and by the ampicillin resistance of all colonies recovered from mouse livers at autopsy. We immunized C57BL/6 mice with three intraperitoneal injections of $5 \times 10^6$ bacteria, either Formalin-killed or live, at 7-day intervals. A week after the last injection the mice were bled and their sera were tested by enzyme-linked immunosorbent assay (ELISA) for reactivity with CTP3 peptide or whole cholera toxin (FIG. 9). We detected antibody to the inserted epitope in all the sera; all sera reacted as strongly with cholera toxin as with the CTP3 peptide.

FIG. 9 shows antibody response of five mice immunized with SL5929, a *Salmonella dublin* live vaccine strain that express the chimeric flagellin genes;□, before immunization, ■, after immunization with SL5929. Reactivity of mouse sera with whole native cholera toxin was measured by solid-phase ELISA (Jacob, C. O. et al., *Proc. Natl. Acad. Sci. USA* 80:7611 (1983)), with peroxidase-conjugated goat antibody to mouse IgG (TAGO). Mice were injected intraperitoneally three times, at weekly intervals, with $5 \times 10^6$ Formalin-killed bacteria; sera were collected 7 days after the last injection. The bars represent the mean optical density for sera from five mice (SE greater than 15% for all dilutions).

Discussion

We demonstrate the expression of epitopes critical to the induction of protective immune responses to pathogenic organisms, as fusion proteins with flagellin, the protein of bacterial flagellar filaments. Several recombinant flagellin genes were constructed which encoded epitopes normally expressed by a protozoan parasite, or by a bacterium. The immunodominant repeating epitope of the circumsporozoite (CS) protein of P. falciparum and the analogous epitope associated with P. berghei were inserted into a region of the H1-d gene of Salmonella muenchen. An oligonucleotide encoding a protective epitope present on the binding subunit of Cholera toxin (CT-B) was also inserted into an H1-d flagellin gene. All of these recombinant constructions were shown to express molecules which migrated through SDS-PAGE gels with mobilities consistent with their expected molecular weights. In addition, these molecules were recognized on Western blots by antisera specific for the H1-d flagellin molecule as well as by reagents which recognize the heterologous epitopes on the native protein.

These hybrid proteins retain their ability to be expressed on the surface of recombinant bacteria thus facilitating isolation and purification of these molecules for use as components of a subunit vaccine. In addition, these molecules were not only expressed by E. coli harboring the recombinant plasmids, but were also introduced into several attenuated Salmonella strains which can be useful as live vaccines. Expression of recombinant flagellin molecules in attenuated, invasive bacteria, can allow the formulation of live vaccines against essentially any pathogen for which critical, immunogenic epitopes can be identified.

EXAMPLE 2

Expression of Epitopes of Hepatitis B Surface Antigen as Recombinant Flagellin Fusion Proteins In this study we inserted two specific HBV S gene sequences encoding respectively amino acid sequences S 122–137 and preS$_2$ 120–145 into the Salmonella flagellin gene H1-d and HBsAg epitopes were shown to be expressed by a flagellin-negative attenuated S. dublin strain transformed by the recombinant plasmids. Immunization of animals with live bacteria led to both anti-HBs and anti-flagellin responses.

Synthetic Oligonucleotides, Synthetic Peptides and Recombinant DNA Methods

Single-stranded oligonucleotides with specific sequence were synthesized and purified by polyacrylamide gel electrophoresis. Synthetic peptides S 122–137 and preS$_2$ 120–145 with sequences corresponding to the synthetic oligonucleotides used were synthesized by the solid phase method of, Erickson, B. W. and Merrifield, R. B., (1976) in The Proteins, eds. H. Neurath and R. L. Hill (Academic Press, New York) Vol 2, pp. 255, and purified by gel filtration on Sephadex LH-20. Purity of the peptides was checked by analytical reverse phase HPLC and amino acid analysis. Cloning techniques were as described by Maniatis, T., et al., 1982, Molecular Cloning: A Laboratory Manual, Cold Spring Harbor Laboratory, Cold Spring Harbor. Bacterial lysates were prepared from 1.0 ml of overnight cultures by centrifuging bacteria and resuspending them in 0.1 ml sample buffer containing 2% SDS (Sigma), 2% B-mercaptoethanol (Sigma), and PMSF (phenylmethanesulfonyl fluoride), TLCK (N-Tosyl-L-lysine chloromethyl ketone), TPCK (N-Tosyl-L-phenylalanine chloromethyl ketone), leupeptin, pepstatin (protease inhibitors, Boehringer Mannheim) at the concentrations suggested by the manufacturers.

Antisera

A polyclonal rabbit anti-H1-d (Salmonella Phase-1 flagellar antigen) serum, received from Dr. P. H. Makela, National Public Health Institute, Helsinki, Finland, was used as an anti-flagellin serum. Polyclonal goat anti-HBs (raised against native HBsAg purified from human plasma) was purchased from Dako company. The antisera against peptides S 122–137 and preS$_2$ 120–145 were raised by immunization of guinea pigs with the respective synthetic peptide conjugated with thyroglobulin. Optimal dilutions of these antisera established by titration were used to detect expression of the respective HBsAg epitopes in bacterial lysates by immunoblotting.

Immunization

Bacterial clones for immunization were grown overnight at 37° C. in Luria-broth containing 50 mg/ml ampicillin. Cells were washed twice and resuspended in phosphate-buffered saline (PBS). Two New Zealand white rabbits were immunized with each bacterial clone by intramuscular injection of 1 ml of a suspension containing approximately $10^9$ live bacteria on days 0, 7, 14, 21 and 28; and blood samples were taken on days 0, 28, 56, and 84.

Three guinea pigs and ten mice (B10.BR mice for preS$_2$ 120–145 clones and BALB/cj mice for S 122–137 clones), the known responder strains for the two peptides (F. Chiasari, personal communication and Milich, D. R. et al., 1986, J. Exp. Med. 164:532) were immunized with each clone by placing approximately $10^9$ live bacteria in 1 ml suspension into the mouth of each guinea pig or approximately $5 \times 10^8$ live bacteria in 0.05 ml in the mouth of each nouse on days 0, 7, 14, and 28; and blood samples were collected on days 0, 28, 56 and 84.

Sera were assayed for specific antibodies by ELISA (Gooderham, K., (1984) in Methods in Molecular Biology, ed. Walker, J. M., Hummang Press, Clifton, N.J., Vol. 1: Proteins, pp. 165) with alkaline phosphatase-conjugated anti-rabbit, anti-rouse, or anti-guinea pig antisera purchased from Boehringer-Mannheim. The antibody titer refers to the highest dilution of test serum at which the ratio of A405 of test serum and A405 of preimmune serum was above 2.0.

Construction of Recombinant Plasmids

Two synthetic oligonucleotides each encoding an HBsAg (subtype ayw) amino acid sequence that appears to contain a protective or partially protective epitope were used in this study (S 122–137 and preS$_2$ 120–145). The upper lines in FIG. 10 represent the nucleotide sequences of the corresponding synthetic oligonucleotides which were designed for insertion in-frame into the EcoRV sites of the flagellin gene (FIG. 10). The codons chosen were the most frequently used in the Salmonella flagellin gene H1-d (Wei, L.-N. and Joys, T. M., 1985, J. Mol. Biol. 186:791). Restriction sites for KpnI and BamHi (for the S 122–147 and preS$_2$ 120–145 coding sequences respectively) were included to allow identification of recombinants by restriction analysis. A half site for EcoRV was put at the 3' end of the preS$_2$ oligonucleotide to facilitate ligation with oligonucleotides for other HBV epitopes. Two stop codons (underlined) were placed in the complementary strand for the preS$_2$ oligonucleotide for easy selection of clones with inserts in the desired orientation. The flagellin gene was contained in plasmid pLS405 consisting of a 3.8 kB S. muenchen genome fragment containing the 1.5 Kb flagellin coding sequence cloned into the EcoRI site of plasmid pUC19 (see Example 1). The central hypervariable region of the wild-type flagellin gene contains two in-frame EcoRV sites with 48 base pairs (bp) apart (FIG. 10).

Deletion of this EcoRV fragment in pLS405, to produce plasmid pLS408, reduces but does not abolish the flagellation of bacteria (see Example 1). Overlapping complementary single-stranded synthetic oligonucleotides were hybridized, phosphorylated, repaired with the Klenow fragment of the *E. coli* DNA polymerase to make blunt end double-stranded DNA fragments, then ligated into EcoRV site of pLS408 with $T_4$ DNA ligase, and the ligation reaction mixture was used to transform CL447, a variant of the flagellin-negative strain *E. coli* C600 hag⁻. Clones with recombinant plasmids were identified by colony hybridization using the respective synthetic oligonucleotide labeled with $^{32}P$ as probe and by restriction digestion. The number, orientation, reading frame and fidelity of inserts was determined by dideoxynucleotide sequencing (Sanger, F., et al., 1977 *Proc. Natl. Acad. Sci. U.S.A.* 74:5463), using a 15 nucleotide synthetic primer corresponding to a flagellin gene sequence about 30 bp downstream of the EcoRV site. Several recombinant plasmids with 1 to 3 copies of the respective synthetic oligonucleotide sequence in different orientations were isolated and further characterized.

Characterization of Recombinant Clones

Recombinant plasmids to be further analyzed were used to transform *S. typhimurium* LB5000 (a restriction-negative, modification proficient and non-flagellated strain with mutation flaA66) competent cells and then transferred to a flagellin-negative live vaccine strain of *S. dublin* SL5928 by transduction using phage P22 HT105/1 int in each case with selection for ampicillin resistance. SL5928 is an aromatic-dependent strain derived from *S. dublin* SL1438 (Smith, B. P., et al., 1984, *Amer. J. Veterin. Sci.* 45:2231); it is non-motile because it is monophasic, with its single flagellin gene inactivated by transposon, Tn10, insertion.

Antigens expressed in both the *E. coli* C600 $hag^-$ variant strain and S15928 were examined by immunblotting using either rabbit anti-H1-d (used as anti-flagellin), or goat anti-HBsAg or anti-synthetic $preS_2$ 120–145 peptide antisera. Bacterial lysates of the *E. coli* C600 $hag^-$ variant transformed with recombinant plasmids containing sequences encoding S 122–137 (S16e and S20e), sequence $preS_2$ 121–145 (ps8e) or sequence for $preS_2$ 120–145 (pS21e), and *S. dublin* SL5928 containing the same plasmids (S16s, S20s and pS8s, pS21s respectively) and controls consisting of lysates of the untransformed *E. coli* C600 $hag^-$ strain and *S. dublin* SL5928, *S. dublin* SL5985 which is SL5928 transformed with only the parent plasmid pLS405 with deletion of the EcORV fragment and HBsAg from a patient serum, were heated to 100° C. for three minutes before loading. Proteins were separated by sodium dodecyl sulfate-12.5% polyacrylamide gel electrophoresis (SDS-PAGE) (Laemmli, U. K., 1970, *Nature* 227:680). The proteins were transferred to nitrocellulose filters which were immunostained with either rabbit anti-flaggelin H1-d antiserum indicated as anti-F or goat anti-HBsAg or rabbit anti-synthetic peptide $preS_2$ 120–145. Incubation with an appropriate second antibody conjugated with either alkaline-phosphatase or peroxidase was followed by reaction with NBT-BCIP (for alkaline-phosphatase) or DAB-$H_2O_2$ (for peroxidase).

As expected, no flagellin antigen was detected in the *E. coli* 600 $hag^-$ variant or in *S. dublin* SL5928, lacking an intact flagellin gene. Two electrophoretic components reacting as flagellin antigen were detected in clone S20 and the basis of this complex pattern is not clear.

Goat anti-HBs raised against HBsAG (ayw) purified from human plasma reacted with the hybrid flagellin proteins of clones S16 and S20 (with the sequence encoding S 122–137) and clones pS8 and pS21 (with the sequence encoding $preS_2$ 121–145 and $preS_2$ 120–145 respectively) indicating that hybrid proteins of these clones contained epitopes recognized by this anti-HBs containing serum.

Rabbit anti-peptide-$preS_2$ 120–145 reacted with the hybrid-flagellin proteins of clones pS8 and pS21 with the $preS_2$ sequence and not with the proteins of any of the clones with the S sequence.

The assembly of recombinant flagellin carrying HBsAg epitopes was investigated by electron microscopy of bacteria expressing the hybrid flagellin. In the motile clone, flagella with morphology indistinguishable from that of wild type flagella were seen on most bacteria. In the three non-motile (as judged by ability to spread on semisolid agar) but flagellin-positive clones S16, pS8, and pS21, very few flagella were observed (data not shown).

FIG. 11 summarizes characteristics of seven recombinant plasmids that have been analysed. The solid (for S sequences) or hatched (for $preS_2$ sequences) arrows represent the orientation and number of synthetic oligonucleotide sequences inserted between the EcoRV sites of the flagellin gene with respect to the orientation of the flagellin gene (represented by the stippled arrows) of pLS405. Bacterial motility was tested using semisolid agar. Rabbits were immunized with *S. dublin* SL5928 transformed with individual plasmids and the antibody responses were measured by ELISA using each synthetic peptide as coating antigen. "nd" represents "not done". As expected, only plasmids with S or $preS_2$ coding sequences in the same orientation as the flagellin gene (S16, S20, pS8, and pS21) led to expression of hybrid flagellin proteins with detectable S or $preS_2$ determinants. Among the small number of plasmids examined, three of the four with an insert in an orientation opposite that of the flagellin gene (S20, S6 and S27) were motile; lysates of bacteria carrying the fourth, pS2, did not bind anti-d antibody, as expected since the $preS_2$ oligonucleotide in reverse orientation includes two termination codons (FIG. 10). Those with one or more inserts in the same orientation and no insert in the opposite orientation (S16, pS8 and pS21) did not spread in semisolid medium although scanty flagella were detected by electron microscopy and both flagellin and HBsAg epitopes were detected by immunoblotting.

Immunogenicity of Bacteria Expressing Hybrid Proteins

The immunogenicity of HBsAg epitopes in the hybrid flagellin proteins was first tested by intramuscular immunization of rabbits with live *S. dublin* SL5928 expressing hybrid flagellin (FIG. 12). FIG. 12 shows antibody responses of rabbits immunized intramuscularly with live *S. dublin* SL5928 transformed with S16 or pS21. Anti-flagellin indicates antibody detected by ELISA with the native flagellin protein purified from SL5928 transformed with the plasmid containing the wild type flagellin gene, anti-peptide represents antibodies detected by ELISA with synthetic peptides S 122–137 and $preS_2$ 120–145 (for animals immunized with SL5928 carrying S16 and pS21 respectively, and anti-HBs represents antibody detected by ELISA with HBsAg produced in CHO cells.

High titers (above $10^4$) of anti-flagellin antibodies were elicited in the two animals receiving SL5928 transformed with plasmid S16 (with sequence encoding S 122–137) and in the two receiving SL5928 transformed with plasmid pS21 (with sequence encoding $preS_2$ 120–145). The ELISA titers of anti-peptide antibodies (anti-S 122–137 or anti-$preS_2$ 120–145 in the respective rabbits immunized with SL5928 carrying the corresponding plasmid) varied between $10^3$ and $2\times10^4$ These antisera reacted with recombinant HBsAg (subtype ayw and containing $preS_2$ sequence) produced in Chinese hamster ovary (CHO) cells (kindly provided by Dr. P. Toillais of Institut Pasteur) (Michel, M. K., et al., 1985, *Biotechnology* 3:561) with peak titers of approximately 6400 in two of four rabbits. The immune sera from these rabbits also reacted strongly with native HBsAg purified from HBv infected chimpanzees detected by Abbott Laboratory's Ausab assay (data not shown). Rabbits immunized with SL5928 transformed with plasmids S20 and pS8 respectively responded similarly (data not shown) to the animals immunized with SL5928 containing S16 and pS21. In two rabbits immunized with SL5928 containing the parental plasmid pLS405 without insertion of HBV sequences, high levels of anti-flagellin antibody were detected as expected, and no anti-S or anti-preS$_2$ peptide or anti-HBsAG antibodies were detected. None of the animals inoculated with this attenuated *S. dublin* mutant (SL5928) manifested signs of septic shock or other illness. These results indicate that the hybrid flagella expressed by *S. dublin* SL5928 carrying the recombinant plasmid contain HBsAg epitopes that are immunogenic and that antibody elicited by them reacts with plasma derived or recombinant HBsAg.

Synthetic peptides S122–137 and preS$_2$ 120–145 specifically blocked the binding of HBsAg produced in CHO cells by antibodies in the immune sera but not the preimmune sera (data not shown) of rabbits immunized with SL5928 clones expressing the S or preS$_2$ epitopes respectively, confirming that the anti-HBs in these animals was directed at epitopes encoded by the sequences introduced into the flagellin gene.

Figure 13:
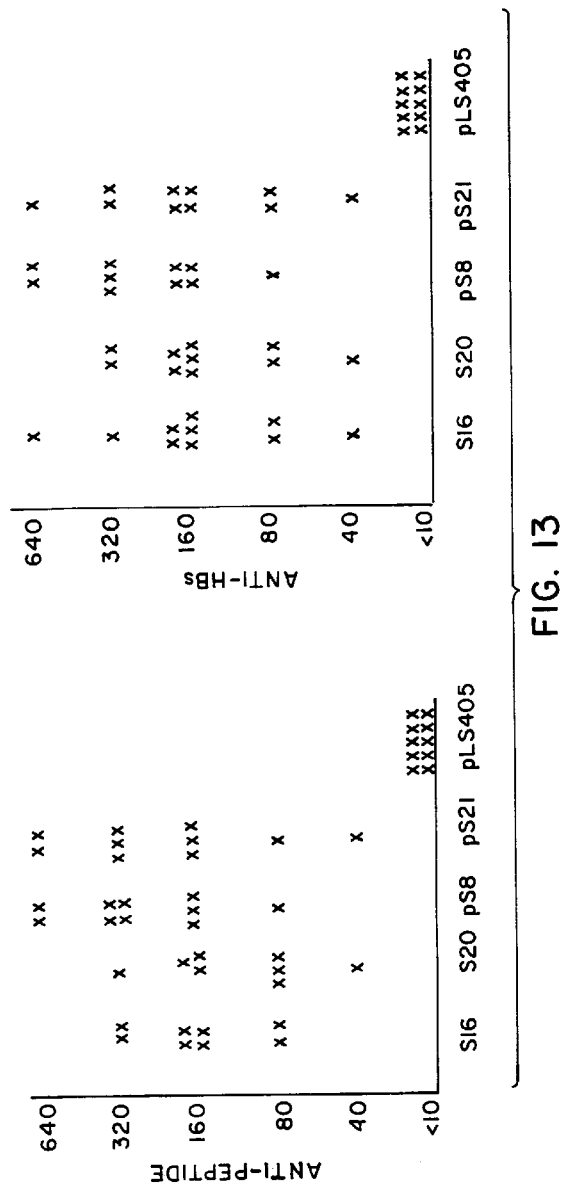
FIG. 13 shows antibody responses in mice immunized orally with live SL5928 expressing an HBsAg epitope. Each "X" represents the titer of antibody of an individual mouse.
Figure 11:
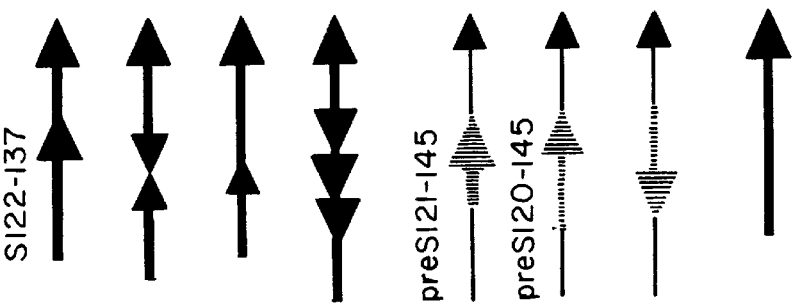
FIG. 11 shows the characteristics of cloned plasmid pLS405 recombinants.
Figure 12:
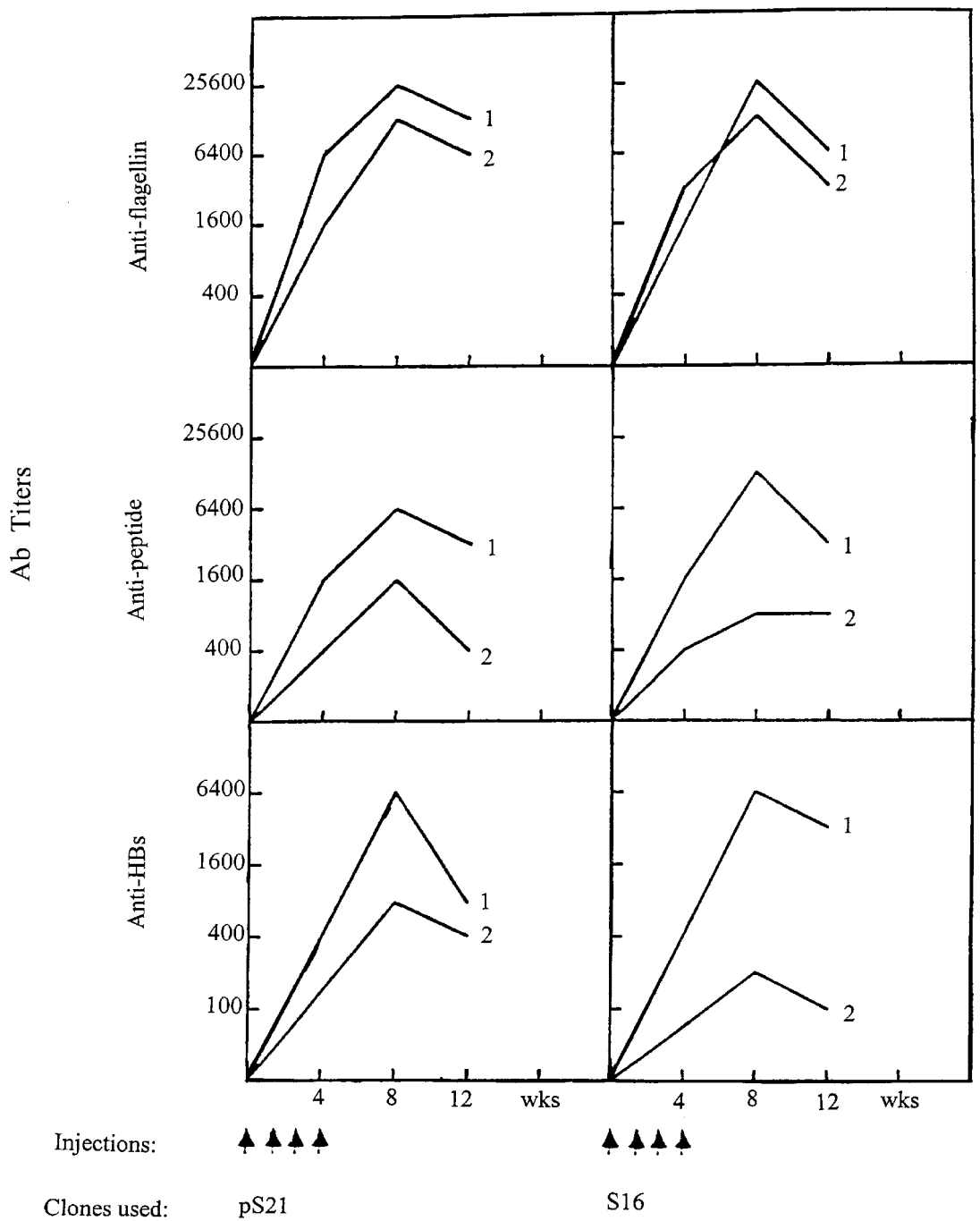
FIG. 12 shows antibody responses of rabbits immunized intramuscularly with live *S. dublin* SL5928 transformed with S16 or pS21.

To determine whether anti-HBs responses would result from oral adminstration of live attenuated *S. dublin* SL5928 expressing hybrid flagella, experiments were carried out in rabbits, mice and guinea pigs. FIG. 13 shows anti-peptide and anti-HBs titers in mice after oral vaccination with SL5928 transformed with each of the recombinant plasmids S16, S20, pS8 and pS21 and with the unaltered flagellin gene pLS405. Significant titers of the respective anti-peptide and anti-HBs were detected in all animals although the titers were lower than those observed after intramuscular immunization of rabbits. Oral adminstration of pLS405 transformed bacteria SL5928 resulted in no detectable anti-HBs or anti-peptide antibody as expected. The titers of anti-peptide and anti-HBs in rabbits and guinea pigs (data not shown) were similar (80 to 640) to those in mice (FIG. 13) after oral administration of live *S. dublin* SL5928. No diarrhea or other disease manifestations were observed in any animal given *S. dublin* SL5928 orally. These experiments indicate that immune responses to HBsAg epitopes are elicited by oral vaccination with live *S. dubin* SL5928 expressing hybrid flagella.

Discussion

In this Example, we have shown that nucleotide sequences encoding antigenic regions of HBsAg polypeptides can be inserted into the hypervariable region of Salmonella flagellin gene and these genes in an attenuated Salmonella mutant can be expressed. Some resulting hybrid flagellin proteins can be assembled into functional flagella as tested by ability to spread in semisolid medium; other hybrid flagellins were not assembled into filaments, except perhaps in a small minority of bacteria. The hybrid flagella contain both flagellin and HBsAg epitopes detected by immunoblotting. The HBsAg epitopes were detected with antisera raised against specific synthetic peptides and against serum-derived HBsAg. Clearly, the number and orientation of HBsAg sequences inserted into the flagellin gene affected the ability of the protein to be assembled into functional flagella. Interestingly, a HBsAg sequence inserted in the same (and not in the opposite) orientation as the flagellin gene reduced bacterial motility suggesting that the specific viral envelope protein sequence (S 122–137) replacing a natural flagellin sequence of the same size significantly altered the conformation of the hybrid flagellin. In addition, replacing the 16 amino acid flagellin deletion with a 27 amino acid insert (preS$_2$ 120–145) did not prevent expression of flagellin but affected its function. In both, HBsAg epitopes recognized by antisera to native HBsAg were detected in the hybrid flagellin protein. These sequences as presented by live bacteria were immunogenic and elicited antibody that recognized native HBsAg. Thus, flagellin represents a bacterial protein in which viral antigens can be presented in a form that is immunogenic in live strains of Salmonella.

EXAMPLE 3

Construction of Recombinant Flaqellin Expressing an Epitope of Rotavirus VP7

Background

The major outer shell polypeptide, VP7, is a glycoprotein with an apparent molecular weight of 38,000 (38.2 K) in its unreduced form and 41,900 (41.9 K) in its reduced form. It has been shown to be the major antigen responsible for inducing neutralizing antibodies to the virus. This glycoprotein is also responsible for virus attachment to cells.

Different serotypes of rotavirus occur and are defined by the neutralizing activity stimulated by VP7. To date, seven serotypes have been identified; four of these (serotypes 1 to 4) are found in humans, and five (serotypes 3 to 7) are found in animals. The importance of these serotypic differences is unclear because recent studies showed that in both animals and man, cross-protection among strains belonging to different serotypes may occur. This cross-protection may occur because there are common antigenic determinants of VP7 which are independent of serotype. Alternatively, the specific amino acid sequences within VP7 (epitopes) responsible for serotype specificity may induce some cross-reactive antibody that is responsible for cross-protection.

Having a molecular weight of 38.2/41.9 K, VP7 is made up of approximately 325 amino acids. The sequence of amino acids comprising VP7 of several different rotavirus isolates has been determined and indicates that the degree of amino acid homology ranges from 75 to 86%. Comparison of the sequences of the VP7's reveal several regions in which the amino acid sequence varies.

Epitope mapping of VP7 using neutralizing monoclonal antibodies localized a neutralizing-absorption domain to a component peptide with an apparent molecular weight of 14,000 (14 K). When purified, this 14 K peptide stimulated the formation of neutralizing antibodies in mice. In addition, it was observed that the secondary structure of this peptide was necessary for maintaining antigenicity. The amino acid sequence of Nebraska calf diarrhea virus (NCDV bovine rotavirus), which exhibits high nucleic acid homology with the C486 bovine rotavirus and is of the same serotype, was used to map the 14 K polypeptide fragment to the region spanning amino acids 165–295. A hydrophilicity plot of the corresponding NCDV glycoprotein identified several hydrophilic regions within this area.

One such region corresponded to amino acid residues 275–295 on VP7 of bovine rotavirus. The corresponding peptide was synthesized by the solid phase peptide synthesis method of Merrifield. The specific amino acid sequence of the peptide was as follows:

Pro—Thr—Thr—Ala—Pro—Gln—Thr—Glu—Arg—
  Met—Met—Arg—Ile—Asn—Trp—Lys—Lys—
  Trp—Trp—Gln—Val.

The purity of this peptide was assessed using thin layer chromatography and reverse phase high performance liquid chromatography. Fast atom bombardment mass spectrometry was used to confirm molecular weight.

The reactivity and specificity of the synthetic peptide was determined by several methods.
1) ELISA with anti-VP7 monospecific serum, indicating specificity of peptide for VP7.
2) ELISA with monoclonal antibodies specific for the neutralizing glycoprotein (VP7) and which had the ability to block virus attachment, indicating specificity of the peptide for a specific region or epitope of VP7.
3) Adsorption blocking assay indicating that the peptide 275–295, blocked virus attachment in vitro to African green monkey cells (MA-104)

Detection of Epitope in Flagellin Construction

To construct hybrid flagellin gene encoding epitope of the rotavirus VP7 (AA 275–292), synthetic oligonucleotides representing amino acids 275–292 of the rotavirus VP7 with the following sequence were inserted into the flagellin expression vector pPX1651 (see Example 1):

```
            275
        A   P   Q   T   E   R   M   M   R
    5'-GCT CCT CAG ACT GAA CGT ATG ATG CGT
    3'-CGA GGA GTC TGA CTT GCA TAC TAC GCA

292
        I   N   W   K   K   W   W   Q   V
    ATC AAC TGG AAA AAA TGG TGG CAG GTT-3'
    TAG TTG ACC TTT TTT ACC ACC GTC CAA-5'
```

Following transformation, recombinants were screened for insertion of the epitope by restriction enzyme mapping, western blotting and nucleotide sequencing. The resulting recombinant plasmid, pROTA92-19, was introduced into *Salmonella dublin* SL5927, and recombinant flagella prepared as described previously.

Flagellin Competition Experiment

The ability of flagellin and flagellin with the rotavirus 275–292 epitope (determined from the VP7 bovine rotavirus sequence as described above) to compete with infectious rotavirus for MA-104 cell receptors was determined. The virus stock used for the competition study was bovine rotavirus strain C486, which was activated with 50 ug trypsin per ml. An appropriate dilution of this stock was used in the competition experiment such that the final number of plaque forming units was 30–50. The initial concentration of the stock flagellin preparation, used as a control, was 3.55 mg/ml, while the stock preparation of flagellin containing the 275–292 epitope was at a concentration of 2.0 mg/ml. Appropriate dilutions of these preparations were made such that the final flagellin concentration was 1.25 ug, 25 ug, 50 ug, or 100 ug per $1\times10^5$ cells.

The competition was carried out by mixing appropriate quantities of rotavirus stock with the appropriate flagellin preparation. The mixtures were adsorbed to MA-104 cell monolayers for 1 h at 37° C. After adsorption, the cell monolayers were washed three times with Eagle's minimal essential media (MEM) and overlayed with 1% agarose beads diluted in MEM. The cells were incubated for 3 days at 37° C. and then stained for detection of plaques with 1% crystal violet diluted in 80% methanol.

Each assay was carried out in triplicate and the flagellin or flagellin containing the 275–292 epitope preparations were also used alone on cell monolayers at the indicated concentrations to control for any adverse effect of the peptides themselves on cell monolayers.

TABLE IV

Percent Plaque Reduction Due to Competition of Flagellin Preparation with Virus

| Preparation | Quantity of Flagellin(ug) | % Reduction[a] |
|---|---|---|
| Flagellin | 1.25 | 0 |
|  | 25.0 | 0 |
|  | 50.0 | 0 |
|  | 100 | 0 |
| Flagellin containing 275–292 | 1.25 | 50 |
|  | 25.0 | 85 |
|  | 50.0 | 99 |
|  | 100 | 100 |

[a]The number of plaque forming units per assay was approximately 40. Each assay was carried out in triplicate and the average of these was used to calculate the final percent reduction.

EXAMPLE 4

Induction of Cellular Immune Responses With Hybrid Flagella Expressing Epitopes of CRM197

Delivery of certain immunogenic epitopes may result in the induction of specific cellular immune responses such as cell proliferation, elaboration of cytokines and specific lysis of target cells expressing those epitopes. In order to demonstrate the capacity of recombinant flagella to induce cellular immune responses, a predicted and experimentally confirmed T cell epitope was employed as a model for these experiments. The epitope which was chosen is comprised of amino acids 366–383 of the CRM197 protein (a mutant Diphtheria toxin molecule). Subsequently, lymph node cells from SJL mice which had been primed previously with CRM197 protein were shown to respond in vitro by incorporation of tritiated thymidine (blastogenesis) when stimulated with purified synthetic peptide representing amino acids 366–383 of the CRM197 protein (see U.S. Ser. No. 07/150,688, filed Feb. 1, 1989, the teachings of which are incorporated herein by reference).

The following oligonucleotides were synthesized encoding CRM197 amino acids 366–383:

```
    366
     N   L   F   Q   V   V   H   N   S   Y   N   R
5'-AAC CTG TTC CAG GTT GTT CAC AAC TCT TAT AAC CGT
3'-TTG GAC AAG GTC CAA CAA GTG TTG AGA ATA TTG GCA

383
  P   A   Y   S   P   G   (S)
CCG GCT TAT TCT CCG G      -3'
GGC CGA ATA AGA GGC CCT AG-5'
```

These oligonucleotides were subcloned into the flagellin expression plasmid pPX1647. This plasmid is a modification of the original vector pPX1651 where the single Bam HI restriction site has been destroyed by cutting, creating flush ends by treatment with Klenow enzyme, and religating, and into which the following oligonucleotide was inserted at the unique EcoRV site:

```
           D   L   L   D   G   S
     5'-GAT ATC ATC GAT GGA TCC-3'
     3'-CTA TAG TAG CTA CCT AGG-5'
```

The underlined codons represent three separate restriction sites, EcoRV, ClaI and BamHI, respectively. This insertion results in the introduction of three unique restriction enzyme recognition sites which facilitate subsequent insertion of sequences encoding foreign epitopes. Plasmid pPX1647 was digested with EcoRV and BamHI, and religated in the presence of an excess amount of the oligonucleotide fragments encoding the CRM197 epitope. Following transformation, recombinants were isolated and characterized by restriction enzyme mapping, western blotting and nucleotide sequencing. The resulting recombinant plasmid, pCRM7F, was introduced into *Salmonella dublin* SL5927, and recombinant flagella prepared as described in Example 1.

Immunization 50 ug of the purified recombinant flagellin preparation was emulsified in an equal volume of complete Freund's adjuvant, and administered to SJL mice s.c. at the base of the tail. As controls, other groups of SJL mice were immunized in a similar fashion with non-recombinant flagella (1650) and purified CRM197 protein, as described in U.S. patent application Ser. No. 07/150,688, filed Feb. 1, 1989.

T-Cell Activation

Murine T-cell proliferation. Inguinal and periaortic lymph nodes were aseptically harvested from mice previously immunized with an optimal dose of antigen emulsified (1:1, vol:vol) in complete Freund's adjuvant. A single cell suspension was prepared in RPMI containing 10% fetal bovine serum. After a single washing, the cells were resuspended in RPMI without serum and counted by trypan blue exclusion with a phase contrast microscope. The cell number was adjusted to a concentration of $3 \times 10^6$ cells/ml in RPMI containing 2% normal mouse serum. Various concentrations of antigens, mitogens or other control materials were prepared in RPMI without serum and aliquoted (0.1 ml) in triplicate into 96 well, flat-bottom tissue culture treated plates. A broad range of doses was routinely employed for all antigens. To these plates, 0.1 ml of cell suspension was added. Thus, the final cell concentration achieved was $3 \times 10^5$ cells/well in media containing 1% mouse serum. After addition of the cells, the cultures were placed in a humidified, 5% $CO_2$ incubator at 37° C. Following 3 days of incubation, the cultures were pulsed for 18 hours with 1 uCi/well of [$^3$H]-thymidine and harvested for counting by liquid scintillation. Thymidine incorporation is expressed as the mean of replicate experimental values minus the mean of replicate non-stimulated (background) values. on-stimulated (background) values.

Results

Figure 14:
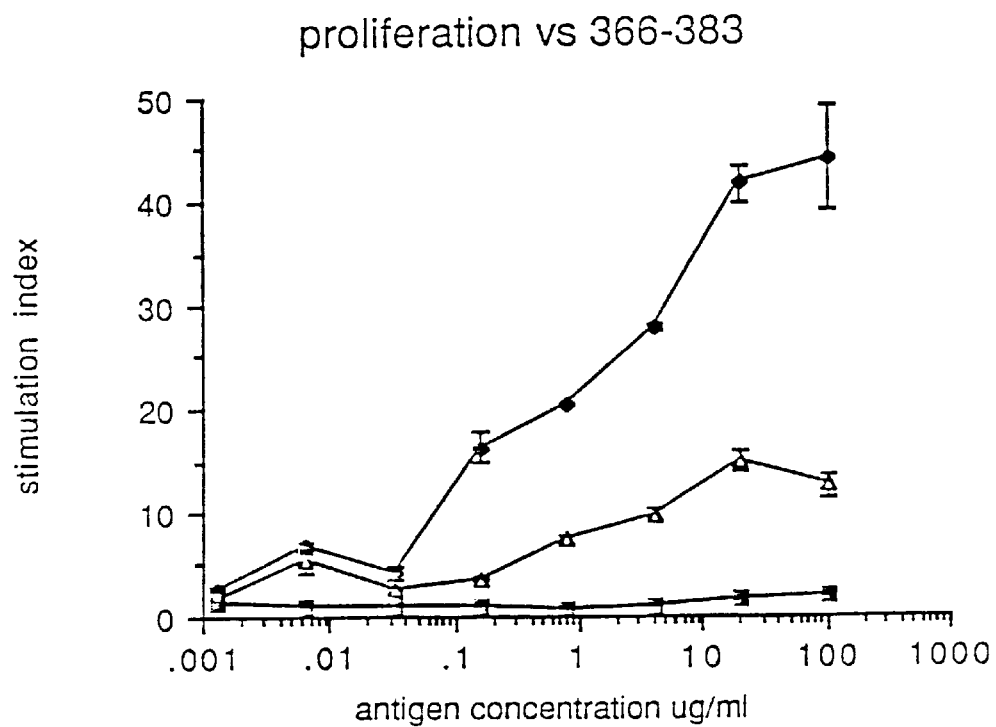
FIG. 14 shows data generated when SJL mice were primed with recombinant flagella, wild type flagella or CRM197 protein, and lymph node cells were restimulated in vitro with purified synthetic peptide encoding amino acids 366–383 of the CRM197 protein.

FIG. 14 shows data generated when lymph node cells of SJL mice were primed with recombinant flagella. SJL mice were immunized with 50ug of purified CRM197 protein (Δ), recombinant flagella encoding the CRM197 366–383 epitope (♦), or purified wild type (1650) flagella (■) in complete Freund's adjuvant s.c. at the base of the tail. Seven days post priming, lymph nodes were removed and single cell suspensions obtained. $3 \times 10^5$ lymph node cells (LNC) were incubated with serial five fold dilutions of purified synthetic peptide encoding amino acids 366–383 of the CRM197 protein. Cells were cultured in RPMI 1640 containing 1% normal mouse serum at 37° C. for three days, pulsed with 1.0 uCi per well of tritiated thymidine for 16 hours, and harvested for liquid scintillation counting. Data is presented as stimulation index (SI) vs. concentration of stimulating antigen where SI=cpm measured in wells in the presence of stimulating antigen divided by cpm in wells in the absence of any stimulating antigen. Each data point represents the mean and standard deviation of triplicate cultures.

Figure 15:
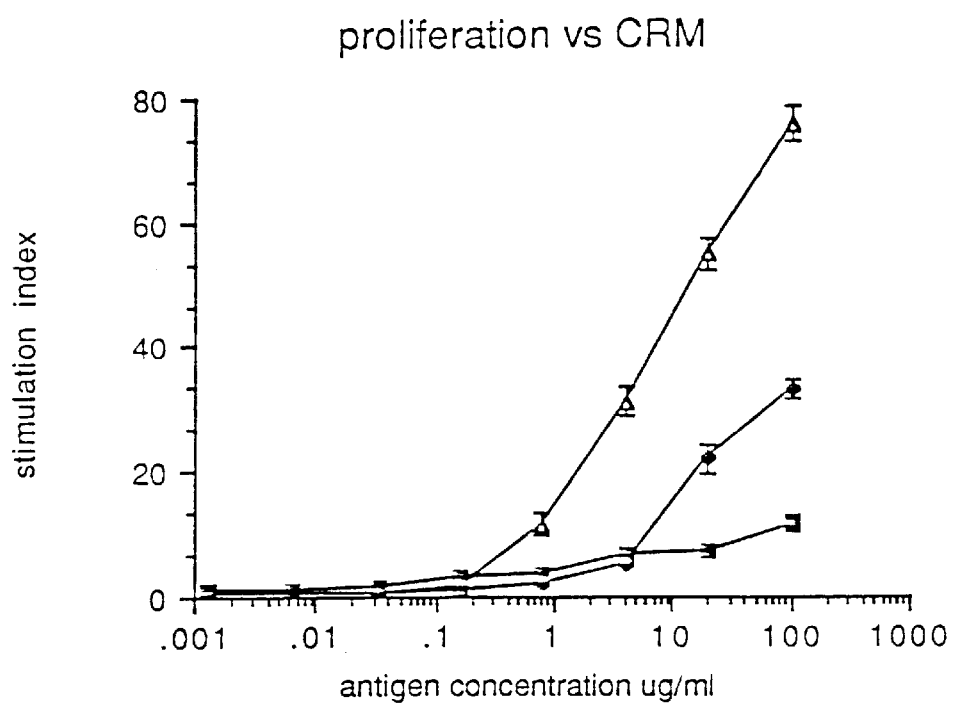
FIG. 15 shows data generated from the priming of lymph node cells as in FIG. 14 which were stimulated with purified CRM197 protein.

FIG. 15 presents data when the same lymph node cells were stimulated with purified CRM197 protein. SJL mice were immunized with 50 ug of purified CRM197 protein (Δ), recombinant flagella encoding the CRM197 366–383 epitope (♦), or purified wild type (1650) flagella (■) in complete Freund's adjuvant s.c. at the base of the tail; under conditions as described for data obtained in FIG. 14.

EXAMPLE 5

The following Tables V and VI summarize the results obtained from motility studies, Western blot analysis and immunization studies using recombinant flagellin fusion proteins in various hosts. The methods for each of the tests summarized below are described in the previous Examples.

TABLE V

Flagellin-Plasmids with Epitope-Specifying Inserts

| Origin | AA Residues Specified | Plasmid Number | Lysate of LB5000/pLS | Host-Plasmid Combinations ||||
|---|---|---|---|---|---|---|---|
| | | | | Host[a] | Combination | Motility | Western Blot | Vaccine Trial |
| Cholera toxin B subunit | CTP3= 50–64 | PLS411 | G2615 | SL1338 | SL5938 | n.a. | + | no |
| | | | | SL5676 | SL5920 | +, b | + | no |
| | | | | SL5928 | SL5929 | +, b | + | yes |
| | | | | SL3261 | SL5939 | n.a. | | no |
| Hepatitis B S Protein | 122–137 −122–137 | S16= pLS414 | G2721 | SL5676 | SL5932 | − | | |
| | | | | SL5928 | SL5934 | − | + | yes |
| Hepatitis B S Protein | 122–137 −137[1] −122[1] | S20= pLS413 | G2624 | SL5676 | SL5924 | + | | |
| | | | | SL5928 | SL5933 | + | + | yes |
| Hepatitis B preS | pS121-145 | pS8= pLS429 | | SL5928 | | − | + | yes |
| Hepatitis B preS | pS120-145 | pS21= pLS428 | | SL5928 | | − | + | yes |
| Hepatitis B preS | pS145[1]= (stop)-120' | pS2 | | SL5928 | | − | − | no |
| HIV Envelope Protein | Kennedy[d] peptide | pLS435 | G2774 | SL5928 | SL7123 | +, b | + | yes |

TABLE V-continued

Flagellin-Plasmids with Epitope-Specifying Inserts

| Origin | AA Residues Specified | Plasmid Number | Lysate of LB5000/ pLS | Host[a] | Host-Plasmid Combinations Combination | Motility | Western Blot | Vaccine Trial |
|---|---|---|---|---|---|---|---|---|
| Streptococcus type 5 M Protein | AVTRGIND-PQRAKEI | pLS439 | G2778 | SL5928 | SL5727 | +, b | + | + | a SL1438 and SL3261 are *S. dublin* and *S. typhimurium*, respectively, both aroA but motile, so that ability of plasmid to cause production of flagella was not testable in them.
b For these combinations, anti-peptide antibody was shown to immobilize.
c[1] $137^1$–$122^1$ indicates the amino acids at sites 122 to 137, which are specified by a DNA sequence for amino acids 122 to 137, inserted in reverse.
d Sequence of HIV gp160 "Kennedy" peptide:

```
       735
        D    R    P    E    G    I    E    E    E    G
5'-   GAT  CGT  CCG  GAA  GGT  ATC  GAA  GAA  GAA  GGT
3'-   CTA  GCA  GGC  CTT  CCA  TAG  CTT  CTT  CTT  CCA

752
        G    E    R    D    R    D    R    S    G
       GGT  GAA  CGT  GAT  CGT  GAT  CGT  TCT  GGT  -3'
       CCA  CTT  GCA  CTA  GCA  CTA  GCA  AGA  CCA  -5'
```

Kennedy et al., 1986, Science 231:1556–59.
Ratner et al., 1985, Nature (London) 313:277–284.

TABLE VI

Immunization Trials

| Epitope | Plasmid | Host | Animal | Dose/No Doses Route/Live, Killed | ELISA +/no. Tested |
|---|---|---|---|---|---|
| Cholera Tox B Subunit | | | | | |
| CTP3 | pLS411 | SL5928 | C57B1/6 | $5 \times 10^6$/x 3/i.p./live | 5/5 |
| CTP3 | pLS411 | SL5928 | C57B1/6 | $5 \times 10^6$/x 3/i.p./HCHO-killed | 5/5 |
| Hepatitis B. Surface Protein | | | | | |
| SAgS16 | pLS414 | SL5928 | Rabbit | $10^9$/x 5/i.m./live | 2/2 |
| | | | Mice BALB.cj | $5 \times 10^8$/x 4/p.o./live | 10/10 |
| | | | Guinea pigs | $10^9$/x 4/p.o./live | 3/3 |
| preS21 | pLS428 | SL5928 | Rabbit | $10^9$/x 5/i.m./live | 2/2 |
| | | | Mice BIO.BR | $5 \times 10^8$/x 4/p.o./live | 10/10 |
| | | | Guinea pigs | $10^9$/x 4/p.o./live | 3/3 |
| S20 | pLS413 | SL5298 | Rabbit | $10^9$/x 5/i.m./live | 2/2 |
| | | | Mice BALB.cj | $5 \times 10^8$/x 4/p.o./live | 10/10 |
| | | | Guinea pigs | $10^9$/x 4/p.o./live | 3/3 |
| pS8 | pLS429 | SL5928 | Rabbit | $10^9$/x 5/i.m./live | 2/2 |
| | | | Mice BIO.BR | $5 \times 10^8$/x 4/p.o./live | 10/10 |
| | | | Guinea pigs | $10^9$/x 4/p.o./live | 3/3 |
| Streptococcus Type 5 M Protein | | | | | |
| Strep. M Prot. | pLS439 | SL5928 | Rabbit | $10^8$/x 3 /i.m./killed | 2/2 |
| | | | Mice BALB/c | $5 \times 10^6$/x 3/i.m./live | 5/5 |
| | | | Mice BALB/c | $10^9$/x 3/p.o./live | 0/5[a] |
| Kennedy Peptide | pLS439 | SL5928 | Rabbit | $10^8$/x 3/i.m./killed | 1/2 |
| | | | Mice BALB/c | $5 \times 10^6$/x 3/i.p./live | 5/5 |

[a]Oral dose may be too low to elicit an immune response.

Deposit of Microorganism

The following bacterial strains, carrying the listed plasmids, have been deposited on May 4, 1988 with the American Type Culture Collection (ATCC), Rockville, Md., and have been assigned the indicated accession numbers:

| Bacterial Strain | Plasmids | Accession Number |
|---|---|---|
| *Salmonella dublin* SL1438 | pPX1650: encoding the full-length H1-d | 67685 |

-continued

| Bacterial Strain | Plasmids | Accession Number |
|---|---|---|
| Salmonella dublin SL1438 | flagellin structural gene of *S. muenchen* pPX1653: encoding 4 copies the 4 amind acid repeat sequence of the sequence of the *Plasmodium falciparum* circumsporozoite protein as a recombinant fusion protein with H1-d flagellin | 67688 |
| Salmonella dublin SL1438 | pPX1662: encoding 4 copies of the 9 amino acid repeat sequence of the *Plasmodium berghei* circumsporozoite protein with H1-d flagellin | 67687 |
| Salmonella dublin 5L1438 | pLS411: encoding the CTP3 peptide of the Cholera toxin B subunit as a recombinant fusion protein with H1-d flagellin | 67686 |
| Salmonella dublin SL5927 | no plasmid (vaccine strain with Tn10 transposon inserted into H1 locus of *Salmonella dublin* SL5927) | 67944 |
| Salmonella dublin SL5927 | pROTA92-19: encoding amino acids 275–292 of the Rotavirus VP7 as a recombinant fusion protein with H1-d flagellin | 67945 |

The present invention is not to be limited in scope by the microorganisms deposited since the deposited embodiments are intended as single illustrations of one aspect of the invention and any microorganisms which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

It is also understood that all base pair sizes given for nucleotides are approximate and are used for purposes of description, and figures which diagrammatically depict dna sequences are not necessarily drawn to scale.

What is claimed is:

1. A recombinant gene comprising a nuclcotide sequence which encodes a flagellin fusion protein, which protein comprises a flagellin sequence containing a first epitope of a Salmonella H1-d flagellin structural gene with at least one epitope of a heterologous organism inserted within the flagellin sequence, wherein the flagellin protein is capable of binding to an antiflagellin antibody, wherein the DNA encoding at least one epitope of the heterologous organism is inserted in place of the DNA which naturally occurs between the natural EcoRV sites of the Salmonella H1-d gene.

2. A plasmid selected from the group consisting of pPX1653, pPX1662, pLS411, and pROTA92-19, as deposited with the ATCC and assigned accession numbers 67688, 67687, 67686, and 67945, respectively.

3. A recombinant microorganism containing a plasmid selected from the group consisting of pPX1653, pPX1662, pLS411, and pROTA92-19, as deposited with the ATCC and assigned accession numbers 67688, 67687, 67686, and 67945, respectively.

* * * * *